US 11,547,581 B2

(12) United States Patent
Byrne et al.

(10) Patent No.: US 11,547,581 B2
(45) Date of Patent: Jan. 10, 2023

(54) ENERGY CONSERVATION OF A MOTOR-DRIVEN DIGIT

(71) Applicant: Touch Bionics Limited, Livingston (GB)

(72) Inventors: Steven Byrne, Edinburgh (GB); Neil Alexander Shaw, Livingston (GB)

(73) Assignee: Touch Bionics Limited, Livingston (GB)

( * ) Notice: Subject to any disclaimer, the term of this patent is extended or adjusted under 35 U.S.C. 154(b) by 131 days.

(21) Appl. No.: 16/721,200

(22) Filed: Dec. 19, 2019

(65) Prior Publication Data

US 2020/0197193 A1 Jun. 25, 2020

Related U.S. Application Data

(60) Provisional application No. 62/782,830, filed on Dec. 20, 2018.

(51) Int. Cl.
*A61F 2/54* (2006.01)
*A61F 2/70* (2006.01)
(Continued)

(52) U.S. Cl.
CPC ............... *A61F 2/586* (2013.01); *A61F 2/72* (2013.01); *B25J 9/102* (2013.01); *B25J 9/126* (2013.01); *B25J 9/1612* (2013.01); *H02P 29/00* (2013.01); *H03K 5/1565* (2013.01); *A61F 2002/6836* (2013.01); *A61F 2002/701* (2013.01);
(Continued)

(58) Field of Classification Search
None
See application file for complete search history.

(56) References Cited

U.S. PATENT DOCUMENTS 2,669,727 A 2/1954 Opuszenski
3,822,418 A 7/1974 Popov et al.
(Continued)

FOREIGN PATENT DOCUMENTS

CN 1803413 7/2006
EP 0 145 504 6/1985
(Continued)

OTHER PUBLICATIONS

International Search Report and Written Opinion in International Application No. PCT/IB2019/061146 dated Apr. 15, 2020 in 11 pages.
(Continued)

*Primary Examiner* — David H Willse
(74) *Attorney, Agent, or Firm* — Knobbe, Martens, Olson & Bear, LLP

(57) ABSTRACT

Routines and methods disclosed herein can increase a power efficiency of a prosthetic hand without drastically reducing the speed at which it operates. A prosthesis can implement an acceleration profile, which can reduce an energy consumption of a motor, or an amount of electrical and/or mechanical noise produced by a motor, as the motor transitions from an idle state to a non-idle state. A prosthesis can implement a deceleration profile, which can reduce the energy consumption of the motor, or an amount of electrical and/or mechanical noise produced by a motor, as the motor transitions from a non-idle state to an idle state.

20 Claims, 14 Drawing Sheets

(51) Int. Cl.
*A61F 2/72* (2006.01)
*A61F 2/58* (2006.01)
*H02P 29/00* (2016.01)
*H03K 5/156* (2006.01)
*B25J 9/10* (2006.01)
*B25J 9/16* (2006.01)
*B25J 9/12* (2006.01)
*B25J 9/18* (2006.01)
*B25J 13/02* (2006.01)
*B25J 15/08* (2006.01)
*A61F 2/76* (2006.01)
*A61F 2/68* (2006.01)

(52) U.S. Cl.
CPC ... *A61F 2002/704* (2013.01); *A61F 2002/763* (2013.01); *A61F 2002/7645* (2013.01)

(56) References Cited

U.S. PATENT DOCUMENTS

| | | | |
|---|---|---|---|
| 3,866,246 | A | 2/1975 | Seamone et al. |
| 4,030,141 | A | 6/1977 | Graupe |
| 4,409,529 | A | 10/1983 | Basford et al. |
| 4,558,704 | A | 12/1985 | Petrofsky |
| 4,623,354 | A | 11/1986 | Childress et al. |
| 4,808,187 | A | 2/1989 | Patterson et al. |
| 4,955,918 | A | 9/1990 | Lee |
| 4,990,162 | A | 2/1991 | LeBlanc et al. |
| 5,246,463 | A | 9/1993 | Giampapa |
| 5,413,611 | A | 5/1995 | Haslam, II et al. |
| 5,888,213 | A | 3/1999 | Sears et al. |
| 5,888,246 | A | 3/1999 | Gow |
| 6,244,873 | B1 | 6/2001 | Hill et al. |
| 6,344,062 | B1 | 2/2002 | Abboudi et al. |
| 6,494,662 | B1 | 12/2002 | De Montalembert |
| 6,589,287 | B2 | 7/2003 | Lundborg |
| 6,660,042 | B1 | 12/2003 | Curcie et al. |
| 6,684,754 | B2 | 2/2004 | Comer |
| 7,056,297 | B2 | 6/2006 | Dohno et al. |
| 7,370,896 | B2 | 5/2008 | Anderson et al. |
| 7,373,721 | B2 | 5/2008 | Bergamasco et al. |
| 7,828,857 | B2 | 11/2010 | Farnsworth et al. |
| 7,922,773 | B1 | 4/2011 | Kuiken |
| 8,197,554 | B2 | 6/2012 | Whiteley et al. |
| 8,396,546 | B2 | 3/2013 | Hirata et al. |
| 8,593,255 | B2 | 11/2013 | Pang et al. |
| 8,662,552 | B2 | 3/2014 | Torres-Jara |
| 8,696,763 | B2 | 4/2014 | Gill |
| 8,821,587 | B2 | 9/2014 | Lanier et al. |
| 8,840,680 | B2 | 9/2014 | Goldfarb et al. |
| 9,034,055 | B2 | 5/2015 | Vinjamuri et al. |
| 9,114,030 | B2 | 8/2015 | van der Merwe et al. |
| 9,121,699 | B2 | 9/2015 | van der Merwe et al. |
| 9,174,339 | B2 | 11/2015 | Goldfarb et al. |
| 9,265,625 | B2 | 2/2016 | Goldfarb et al. |
| 9,278,012 | B2 | 3/2016 | Gill |
| 9,402,749 | B2 | 8/2016 | Gill et al. |
| 9,463,100 | B2 | 10/2016 | Gill |
| 9,720,515 | B2 | 8/2017 | Wagner et al. |
| 9,730,815 | B2 | 8/2017 | Goldfarb et al. |
| 9,826,933 | B2 | 11/2017 | van der Merwe et al. |
| 9,901,465 | B2 | 2/2018 | Lanier, Jr. et al. |
| 9,931,230 | B2 | 4/2018 | Sikdar et al. |
| 10,265,197 | B2 | 4/2019 | Gill et al. |
| 10,318,863 | B2 | 8/2019 | Lock et al. |
| 10,369,024 | B2 | 8/2019 | Gill |
| 10,398,576 | B2 | 9/2019 | Gill et al. |
| 10,610,385 | B2 | 4/2020 | Meijer et al. |
| 11,185,426 | B2 | 11/2021 | Gill et al. |
| 2003/0036805 | A1 | 2/2003 | Senior |
| 2003/0191454 | A1* | 10/2003 | Niemeyer ............ A61B 34/30 606/1 |
| 2004/0103740 | A1 | 6/2004 | Townsend et al. |
| 2005/0192677 | A1 | 9/2005 | Ragnarsdottir et al. |
| 2006/0158146 | A1 | 7/2006 | Tadano |
| 2006/0167564 | A1 | 7/2006 | Flaherty et al. |
| 2006/0212129 | A1 | 9/2006 | Lake et al. |
| 2008/0058668 | A1 | 3/2008 | Seyed Momen et al. |
| 2008/0146981 | A1 | 6/2008 | Greenwald et al. |
| 2008/0215162 | A1 | 9/2008 | Farnsworth et al. |
| 2008/0262634 | A1 | 10/2008 | Puchhammer |
| 2009/0302626 | A1 | 12/2009 | Dollar et al. |
| 2010/0016990 | A1 | 1/2010 | Kurtz |
| 2010/0036507 | A1 | 2/2010 | Gow |
| 2010/0116078 | A1 | 5/2010 | Kim |
| 2010/0274365 | A1 | 10/2010 | Evans et al. |
| 2010/0328049 | A1 | 12/2010 | Frysz et al. |
| 2011/0136376 | A1 | 6/2011 | Johnson et al. |
| 2011/0257765 | A1 | 10/2011 | Evans et al. |
| 2011/0264238 | A1 | 10/2011 | van der Merwe et al. |
| 2012/0061155 | A1 | 3/2012 | Berger et al. |
| 2012/0123558 | A1 | 5/2012 | Gill |
| 2012/0221122 | A1 | 8/2012 | Gill et al. |
| 2012/0280812 | A1 | 11/2012 | Sheikman et al. |
| 2012/0286629 | A1 | 11/2012 | Johnson et al. |
| 2012/0330439 | A1 | 12/2012 | Goldfarb et al. |
| 2013/0053984 | A1 | 2/2013 | Hunter et al. |
| 2013/0253705 | A1 | 9/2013 | Goldfarb et al. |
| 2014/0324189 | A1 | 10/2014 | Gill et al. |
| 2014/0371871 | A1 | 12/2014 | Farina et al. |
| 2015/0142082 | A1 | 5/2015 | Simon et al. |
| 2015/0216681 | A1 | 8/2015 | Lipsey et al. |
| 2015/0328019 | A1 | 11/2015 | Park et al. |
| 2015/0351935 | A1 | 12/2015 | Donati et al. |
| 2015/0374515 | A1 | 12/2015 | Meijer et al. |
| 2016/0120664 | A1 | 5/2016 | Schultz |
| 2016/0143751 | A1 | 5/2016 | Chestek et al. |
| 2016/0166409 | A1 | 6/2016 | Goldfarb et al. |
| 2016/0287422 | A1 | 10/2016 | Kelly et al. |
| 2017/0049583 | A1 | 2/2017 | Belter et al. |
| 2017/0049586 | A1 | 2/2017 | Gill et al. |
| 2017/0203432 | A1 | 7/2017 | Andrianesis |
| 2017/0209288 | A1 | 7/2017 | Veatch |
| 2017/0340459 | A1 | 11/2017 | Mandelbaum |
| 2018/0014744 | A1 | 1/2018 | Duerstock et al. |
| 2018/0116829 | A1 | 5/2018 | Gaston et al. |
| 2018/0168477 | A1 | 6/2018 | Graimann et al. |
| 2018/0221177 | A1 | 8/2018 | Kaltenbach et al. |
| 2018/0235782 | A1 | 8/2018 | Choi et al. |
| 2018/0256365 | A1 | 9/2018 | Bai |
| 2019/0216618 | A1 | 7/2019 | Gill |
| 2020/0054466 | A1 | 2/2020 | Gill et al. |
| 2020/0268532 | A1 | 8/2020 | Meijer et al. |

FOREIGN PATENT DOCUMENTS

| | | |
|---|---|---|
| EP | 1 043 003 | 10/2000 |
| EP | 2 114316 | 7/2014 |
| EP | 2 125 091 | 4/2016 |
| EP | 2467101 | 4/2016 |
| EP | 2 696 814 | 1/2017 |
| GB | 1 585 256 | 2/1981 |
| GB | 2 444 679 | 6/2008 |
| JP | 53-011456 | 2/1978 |
| JP | 2001-082913 | 3/2001 |
| WO | WO 95/024875 | 9/1995 |
| WO | WO 00/069375 | 11/2000 |
| WO | WO 02/049534 | 6/2002 |
| WO | WO 03/017878 | 3/2003 |
| WO | WO 03/017880 | 3/2003 |
| WO | WO 2006/069264 | 6/2006 |
| WO | WO 2006/078432 | 7/2006 |
| WO | WO 2006/086504 | 8/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044207 | 4/2008 |
| WO | WO 2008/098059 | 8/2008 |
| WO | WO 2008/098072 | 8/2008 |
| WO | WO 2010/018358 | 2/2010 |
| WO | WO 2010/149967 | 12/2010 |

(56) References Cited

FOREIGN PATENT DOCUMENTS

| WO | WO 2011/001136 | 1/2011 |
|---|---|---|
| WO | WO 2011/022569 | 2/2011 |
| WO | WO 2011/036473 | 3/2011 |
| WO | WO 2011/036626 | 3/2011 |
| WO | WO 2011/107778 | 9/2011 |
| WO | WO 2014/111843 | 7/2014 |
| WO | WO 2017/137930 | 8/2017 |
| WO | WO 2018/054945 | 3/2018 |
| WO | WO 2018/132711 | 7/2018 |
| WO | WO 2018/178420 | 10/2018 |
| WO | WO 2018/218129 | 11/2018 |
| WO | WO 2021/124060 | 6/2021 |

OTHER PUBLICATIONS

Antonio et al., "A Virtual Upper Limb Prosthesis as a Training System", 7th International Conference on Electrical Engineering, Computing Science and Automatic Control (CCE 2010) Tuxtla Gutiérrez, Chiapas, México. Sep. 8-10, 2010, pp. 210-215.

Baek et al., "Design and Control of a Robotic Finger for Prosthetic Hands", Proceedings of the 1999 IEEE International Conference on Intelligent Robots and Systems, pp. 113-117.

Butterfaß et al., "DLR-Hand II: Next Generation of a Dextrous Robot Hand", IEEE International Conference on Robotics and Automation, Seoul, Korea, May 21 -26, 2001, vol. 1, pp. 109-114.

Connolly, "Prosthetic Hands from Touch Bionics", Industrial Robot, Emerald Group Publishing Limited, Jun. 2008, vol. 35, No. 4, pp. 290-293.

Cotton et al., "Control Strategies for a Multiple Degree of Freedom Prosthetic Hand", Measurement + Control, Feb. 2007, vol. 40, No. 1, pp. 24-27.

"DC Circuit Theory", https://www.electronics-tutorials.ws/dccircuits/dcp_1.html, Date verified by the Wayback Machine Apr. 23, 2013, pp. 16.

Dellorto, Danielle, "Bionic Hands Controlled by iPhone App", CNN, Apr. 12, 2013, pp. 4 http://www.cnn.com/2013/04/12/health/bionic-hands.

"DsPIC Microcontrollers Introduction and Features", https://microcontrollerslab.com/dspic.microcontrollers-introduction/, Aug. 1, 2017, pp. 4.

"DuPont Engineering Design—The Review of DuPont Engineering Polymers in Action", http://www.engpolymer.co.kr/x_data/magazine/engdesign07_2e.pdf, Feb. 2007, pp. 16.

Edsinger-Gonzales, Aaron, "Design of a Compliant and Force Sensing Hand for a Humanoid Robot", 2005, pp. 5.

Fildes, Jonathan, "Bionic Hand Wins Top Tech Prize", BBC News, Jun. 9, 2008, http://news.bbc.co.uk/2/hi/science/nature/7443866.stm, pp. 3.

Fukuda et al., "Training of Grasping Motion Using a Virtual Prosthetic Control System", 2010 IEEE International Conference on Systems Man and Cybernetics (SMC), Oct. 10-13, 2010, pp. 1793-1798.

Gaiser et al., "A New Anthropomorphic Robotic Hand", 2008 8th IEEE-RAS International Conference on Humanoid Robots, Dec. 1-3, 2008, Daejeon, Korea, pp. 418-422.

Grip Chips™, Datasheet, May 15, 2014, Issue 1, http://touchbionics.com/sites/default/files/files/Grip%20Chip%20datasheet%20May%202014.pdf, pp. 1.

"ILimb Bionic Hand Now Ready for Market", Technovelgy.com, www.technovelgy.com/ct/Science-Fiction-News.asp?NewsNum=1125, as printed Jul. 6, 2020 in 3 pages.

Kargov et al., "Applications of a Fluidic Artificial Hand in the Field of Rehabilitation", Rehabilitation Robotics, Ch. 15, Aug. 2007, pp. 261-286.

Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.

Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.

Kawasaki et al., "Design and Control of Five-Fingered Haptic Interface Opposite to Human Hand", IEEE Transactions on Robotics, Oct. 2007, vol. 23, No. 5., pp. 909-918.

Kim et al., "Development of Anthropomorphic Prosthesis Hand $H^3$ and its Control", 4th WSEAS/IASME International Conference on Dynamical Systems and Control (Control'08) Corfu, Greece, Oct. 26-28, 2008, pp. 133-138.

Kyberd et al., "Two-Degree-of-Freedom Powered Prosthetic Wrist", Journal of Rehabilitation Research & Development, Jul. 2011, vol. 48, No. 6, pp. 609-617.

Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.

Lotti et al., "UBH 3: A Biologically Inspired Robotic Hand", Jan. 2004, pp. 7.

Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.

Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.

MEC '05: Integrating Prosthetics and Medicine, University of New Brunswick's MyoElectric Controls/Powered Prosthetics Symposium, Aug. 17-19, 2005, Fredericton NB Canada, pp. 260.

Osborn et al., "Utilizing Tactile Feedback for Biomimetic Grasping Control in Upper Limb Prostheses", Department of Biomedical Engineering, Johns Hopkins University, Baltimore, USA, Nov. 5, 2013, pp. 4.

Pedrocchi et al., "MUNDUS Project: Multimodal Neuroprosthesis for Daily Upper Limb Support", Journal of Neuroengineering and Rehabilitation, Jul. 2013, vol. 10, No. 66, pp. 20.

Poppe, Zytel HTN Provides a Helping Hand, DuPont Engineering Design 8 (2007), pp. 3.

Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.

Puig et al., "A Methodology for the Design of Robotic Hands with Multiple Fingers", International Journal of Advanced Robotic Systems, 2008, vol. 5, No. 2, pp. 177-184.

Pylatiuk et al., "Design and Evaluation of a Low-Cost Force Feedback System for Myoelectric Prosthetic Hands", 18 J. Prosthetics and Orthotics 57-61 (2006).

Pylatiuk et al., "Results of an Internet Survey of Myoelectric Prosthetic Hand Users", Prosthetics and Orthotics International, Dec. 2007, vol. 31, No. 4, pp. 362-370.

Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.

Stix, Gary, "Phantom Touch: Imbuing a Prosthesis with Manual Dexterity", Scientific American, Oct. 1998, pp. 41 & 44.

"Supro Wrist", Touch Bionics, https://web.archive.org/web/20160928141440/http://www.touchbionics.com/products/supro-wrist as archived Sep. 28, 2016 in 3 pages.

"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.

Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).

Touch Bionics PowerPoint Slide in 1 page, believed to be presented at Advanced Arm Dynamics company Jan. 11, 2016. (Applicant

(56) References Cited

OTHER PUBLICATIONS requests that the Examiner consider this reference as qualifying as prior art as of the date indicated, but Applicant does not admit its status as prior art by submitting it here and reserves the right to challenge the reference's prior art status at a later date).

Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).

Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.

Vilarino, Martin, "A Novel Wireless Controller for Switching among Modes for an Upper-Limb Prosthesis", The Academy Today, Jan. 2014, vol. 10, No. 1, pp. A-12 to A-15.

Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.

"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.

Schulz et al., "Die Entwicklung Einer Multifunktionalen Kosmetischen Handprothese", Prothetik, Orthopädie-Technik, Aug. 2006, pp. 627-632, (total pages 6).

The Weir Thesis ("Weir Thesis") is entitled "An Externally-Powered, Myo-Electrically Controlled Synergetic Prosthetic Hand for the Partial-Hand Amputee", published Aug. 1989, pp. 1722-2086 (page numbers on bottom right of page), (total pages 365).

Ward, Derek Kempton, "Design of a Two Degree of Freedom Robotic Finger", Sep. 1996, pages: Title Page, i-xviii, 1-92, 95-119, Unnumbered Appendix F (19 pages), (total pages 155).

Weir et al., "A Myoelectrically Controlled Prosthetic Hand forTransmetacarpal Amputations", JPO Journal of Prosthetics and Orthotics, Jun. 2001, vol. 13, No. 2, pp. 26-31, (total pages 6).

* cited by examiner

ENERGY CONSERVATION OF A MOTOR-DRIVEN DIGIT

CROSS-REFERENCE TO RELATED APPLICATIONS

This application claims the benefit of U.S. Provisional Patent Application No. 62/782,830, filed Dec. 20, 2018, entitled ENERGY CONSERVATION OF A MOTOR-DRIVEN DIGIT, the disclosure of which is hereby incorporated herein by reference in its entirety for all purposes.

The concepts described in this application are compatible with and can be used in conjunction with any combination of the embodiments and/or features described in U.S. patent application Ser. No. 16/219,556 (the '556 application), filed Dec. 13, 2018, entitled "POWERED PROSTHETIC THUMB," the disclosure of which is hereby incorporated herein by reference in its entirety for all purposes. Some or all of the features described below can be used or otherwise combined together with any of the features described in the '556 application.

TECHNICAL FIELD

The present disclosure relates to prosthetics. More specifically, this disclosure relates to systems, methods, and apparatuses for reducing electrical noise and/or reducing energy consumption in a motor-driven digit of a prosthesis.

BACKGROUND

Over the years, many kinds of prostheses have been devised in effort to replace the limbs that amputees have lost. In particular, efforts have been made to develop prostheses that will replace the loss of major limbs such as legs and arms in view of the immense impact that such a loss has on the amputee. The loss of upper limbs creates particular challenges due to the intricacy and dexterity of the human hand.

To that end, electric motors have been incorporated into some prostheses to facilitate movements of one or more of the digits, such as prosthetic thumbs or fingers. However, an electric motor can introduce undesirable electrical noise into an associated prosthesis. Furthermore, an electric motor can consume a significant amount of energy. Improvements in this area are therefore desirable.

SUMMARY

The following disclosure describes non-limiting examples of some embodiments. For instance, other embodiments of the disclosed systems and methods may or may not include the features described herein. Moreover, disclosed advantages and benefits can apply only to certain cases of the invention and should not be used to limit the disclosure. The embodiments disclosed herein each have several aspects no single one of which is solely responsible for the disclosure's desirable attributes.

The present disclosure describes example systems, methods, and apparatuses for increasing power efficiency of a prosthetic hand without significantly reducing the speed at which it operates. A prosthesis can implement an acceleration profile, which can reduce an energy consumption of a motor, or an amount of electrical and/or mechanical noise produced by a motor, as the motor transitions from an idle state to a non-idle state. A prosthesis can implement a deceleration profile, which can reduce the energy consumption of the motor, or an amount of electrical and/or mechanical noise produced by a motor, as the motor transitions from a non-idle state to an idle state.

DETAILED DESCRIPTION

Although certain cases and examples are described below, it will be understood that the disclosure extends beyond the specifically disclosed embodiments and/or uses and obvious modifications and equivalents thereof. Thus, it is intended that the scope of the disclosure herein disclosed should not be limited by any particular embodiments described below.

Amputees prefer prosthetic hands that have a long battery life and that mimic, as close as possible, the natural movement of a sound hand, including the speed at which a sound hand can react or move into a particular hand grip. However, in general, the battery life of a prosthetic hand is inversely related to the speeds of the motors of the prosthetic hand. Accordingly, it can be difficult to navigate the compromise between a speed of the prosthetic hand and its power consumption.

Routines and methods disclosed herein can increase a power efficiency of a prosthetic hand without significantly reducing the speed at which it operates. For example, routines and methods disclosed herein can implement an acceleration profile, which can reduce the energy consumption of a motor as the motor transitions from an idle state to a non-idle state. As another example, routines and methods disclosed herein can implement a deceleration profile, which can reduce the energy consumption of a motor as the motor transitions from a non-idle state to an idle state. Furthermore, in some cases, routines and methods disclosed herein can reduce an amount of electrical and/or mechanical noise produced by a motor as the motor transitions from an idle state to a non-idle state or a non-idle state to an idle state.

Prosthesis Overview

Figure 1:
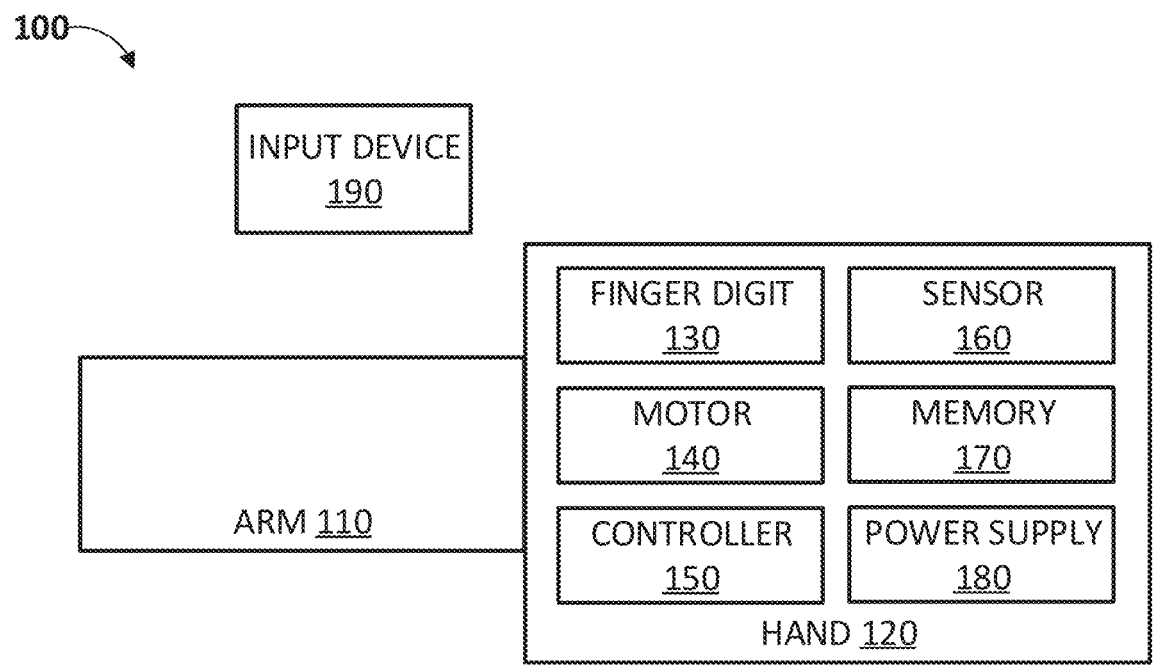
FIG. 1 illustrates a block diagram of an example prosthesis.

FIG. 1 illustrates an example block diagram of an example prosthesis 100.

In the illustrated example, the prosthesis 100 includes an arm 110 attached to a hand 120. The arm 110 may be a prosthetic arm or may be a natural arm, i.e. a natural or sound human arm. Alternatively, the arm 110 may be a stump or include a fitting on a distal end thereof. The hand 120 may be a prosthetic hand, for example, a full prosthetic hand or a partial prosthetic hand and may include one or more finger digits 130, motors 140, controllers 150, sensors 160, data stores 170, and/or power supplies 180.

Any of the finger digit(s) 130, motor(s) 140, controller(s) 150, sensor(s) 160, data store(s) 170, and/or power supply(ies) 180 can be in electrical communication. For example, the controller(s) 150 can communicate with any of the motor(s) 140, sensor(s) 160, data store(s) 170, power supply(ies) 180, and/or input device(s) 190, among other components. Depending on the embodiment, the finger digit(s) 130, motor(s) 140, controller(s) 150, sensor(s) 160, data store(s) 170, and/or power supply(ies) 180 can be located in a number of locations including any location in or on the arm 110 or hand 120, remote from the arm 100 and hand 120, attached to the wearer of the prosthesis 100 or the like. Furthermore, it will be understood that some of these separate components may be combined in a variety of ways to achieve particular design objectives. For example, in some cases, the data store 170 may be combined with controller 150 components to save cost and/or improve performance. Furthermore, the prosthesis 100 can include few or more components, as desired, such as one or more input device(s) 190.

The one or more finger digits 130 can correspond to one or more of an index finger, a middle finger, a ring finger, a pinky finger, or a thumb. In some cases, the hand 120 can include more than four finger digits 130. In some cases, the hand 120 can include fewer than four finger digits 130, for example, where the hand 120 is a partial prosthetic hand. In instances such as these, the hand 120 can include a structure, such as a palm structure, attaching the one or more finger digits together or with the arm 110. In some cases, the hand 120 may not include a structure, such as a palm structure. For example, one or more of the finger digits may connect directly together or connect directly with the arm 110. In some cases, a finger digit 130 corresponding to a thumb can be separate from but attached to a partial prosthetic hand. The partial prosthetic hand can attach to a natural, partial hand having one or more natural fingers, which can attach to a natural arm. The one or more finger digits 130 can be individually or collectively referred to as a finger digit 130, finger digit(s) 130 or finger digits 130.

The finger digit 130 can allow for movement in a natural manner and through large or small ranges of motion manner, for example by providing rotation about one or multiple axes, simultaneous rotation about multiple axes, or rotation about one or more moving axes, among other advantages, for example as further described in the '556 application, which was previously incorporated by reference.

Returning to FIG. 1, the prosthesis 100 can include one or more motors for moving the finger digit 130. For example, in some cases, the prosthesis 100 includes a separate motor for each finger digit 130. As another example, the prosthesis 100 can include a set of one or more separate motors for each finger digit 130. Still, as another example, the prosthesis 100 can include six motors, such as two motors for a finger digit 130 associated with a thumb and separate motors for each finger digit 130 associated each of the index finger, middle finger, ring finger, and pinky finger. The one or more motors of the prosthesis 100 can be individually or collectively referred to as motor 140, motor(s) 140, or motors 140.

The prosthesis 100 can include or be in communication with one or more sensors 160, which can individually or collectively be referred to as sensor 160, sensor(s) 160, or sensors 160. The sensors 160 can capture information relating to position, speed, acceleration, orientation, torque, current, voltage, force, or movement of the prosthesis 100. The sensor data may be processed in real-time or near real-time by the sensor(s) 160 or a processing device of the prosthesis 100, such as the controller 150. The sensor(s) 160 can include, but are not limited to, a torque sensor, current sensor, voltage sensor, force sensor, acceleration or orientation sensor, or position sensor. The sensor(s) 160 can be located in any number of locations in or on the prosthesis 100, in or on one a wearer of the prosthesis 100, or remote from the prosthesis 100.

A torque sensor of the sensors 160 can capture information relating to a torque of a motor 140. A current sensor of the sensors 160 can capture information relating to one or more currents flowing through the prosthesis 100, such as a current drawn by a motor 140 or a current flowing from the power supply 180. A voltage sensor of the sensors 160 can capture information relating to one or more voltages of the prosthesis 100, such as a voltage received by a motor 140 or a voltage of the power supply 180.

A torque sensor can be configured to measure a component of force applied to the prosthesis 100 from the ground or other supporting surface in a direction substantially along or parallel to a shin longitudinal axis. In some cases, the force sensor can be implemented as a load cell.

Data from the sensors 160 can be received by the controller 150 can used to determine various parameters associated with the prosthesis 100, such as a torque of a motor 140 or whether a motor-stall-threshold is satisfied, described further below.

An acceleration or orientation sensor of the sensors 160 can capture information relating to position, speed, acceleration, or orientation of the prosthesis 100, such as position, speed, acceleration, or orientation data relating to any of the arm 110, the hand 120, or the finger digit 130. In some instances, the acceleration or orientation sensor can capture information corresponding to in multiple axes, such as two or three substantially mutually perpendicular axes. In some cases, the acceleration or orientation sensor can be implemented as one or more of an accelerometer, an orientation sensor, a gravity sensor, or a gyroscope.

Data from the acceleration or orientation sensor can be received by the controller 150 can used to determine various parameters associated with the prosthesis 100, such as an acceleration of the finger digit 130, a deceleration of the finger digit 130, an orientation of the finger digit 130, an orientation of the prosthesis 100, a torque of a motor 140, a position of the finger digit 130, or the like.

A force sensor of the sensor(s) 160 can capture information relating to a force applied on or by the finger digit 130. For example, the finger digit 130 or portions thereof (e.g., finger-pads of the finger digit 130) can be fitted with capacitive or inductive force sensors. The force sensor can be configured to measure a component of force applied to the finger digit 130 by an object or other external force in one or more directions. In some cases, the force sensor 112 can be implemented as a load cell.

Force measurement data from the force sensor can be received by the controller 150 and can be used to determine various parameters associated with the prosthesis 100, such as a force applied to the finger digit 130, a torque of a motor 140, a position of the finger digit 130, or the like. For example, using the force measurement data, the controller 150 can determine whether the finger digit 130 is touching an object or other opposing force as it is moved by a motor 140.

A position sensor of the sensor(s) 160 can capture information relating to position of the finger digit 130, such as an absolute position of the finger digit 130. In some cases, the position sensor of the sensor(s) 160 can be implemented as a Hall Effect sensor. For example, the motor 140 or the finger digit 130 can include a magnet, such as a magnet about 0.5 to 5 mm in diameter or about 1 mm or 2 mm in diameter, and the magnet may be positioned on a rotating link of the motor 140 or the finger digit 130. As the link rotates, the distance between the magnet and the Hall Effect sensor changes. The Hall Effect sensor can sense the magnet, and the Hall Effect sensor can provide signals with different levels of current output depending on the proximity of a magnetic field. The magnetic field changes as the distance from the magnet changes. By calibrating the variation of the signaled current by the Hall Effect sensor versus an associated angle that the finger digit 130 or portions thereof rotates, the controller 150 can use the signals the Hall Effect sensor to determine the angular position of the finger digit 130 or portions thereof.

In some cases, a position sensor of the sensor(s) 160 can be implemented as a potentiometer, which may be used to obtain the absolute position of the finger digit 130. In some cases, an incremental optical rotary encoder and/or gyro sensor may be used to control the finger digit 130. For example, an incremental optical rotary encoder can generate a signal when a motor 140 moves. The motor 140 may include absolute optical encoders. For example, the motor 140 may include absolute optical encoders that monitor an internal position of the motor 140. In some cases, the controller 150 can derive the position of the finger digit 130 based at least in part on the motor's rotation.

Position data from sensor(s) 160 can be received by the controller 150 and can be used to determine various parameters associated with the prosthesis 100, such as an absolute position, a relative position, or an angular position of the finger digit 130.

The sensor(s) 160 can be located in any one or more locations, including any location in or on the arm 110, hand 120, or remote from the arm 100 or hand 120.

The prosthesis 100 can include or be in communication with one or more input devices (which can be individually or collectively referred to as input device(s) 190). The input device(s) 190 can capture or receive user input and can transmit signals to the prosthesis 100, such as the controller 150, based at least in part on the user input.

As an example, the input device(s) 190 can include one or more myoelectric electrodes. A myoelectric electrode can detect electric activity from a muscle of a wearer of the prosthesis 100 (for example, muscles in the wearer's forearm), and the myoelectric electrode can relay information associated with that activity to the controller 150. As another example, the input device(s) 190 can include a pressure sensitive resistor. As another example, the input device(s) 190 can detect activity associated with the wearer of the prosthesis 100, such as signals derived from one or more neural implants in the wearer of the prosthesis or orthosis, electromyography (EMG) activity from reinnervated muscles, muscles of the feet and/or chest, or the like. The input device(s) 190 can relay information associated with that activity to the controller 150. The relayed information can be in the form of one or more activation signals. The controller 150 can communicate command signals to the motor(s) 140 based at least in part on the one or more activation signals received from the input device(s) 190.

The input device(s) 190 can include a switch, such as a toggle switch, a push button switch, a rotary switch, or the like. The user can interact with the switch or another input device to control the operation of the prosthesis, such as the movement of the finger digit 130. The switch can be toggled or interacted with by a user, causing one or more activation signals to be relayed to the controller 150. The controller 150 can communicate command signals to the motor(s) 140 based at least in part on the one or more activation signals received from the input device(s) 190.

The power supply 180 can be electrically coupled and/or supply power to the motor(s) 140. As described herein, a motor 140 can use energy supplied by the power supply 180 to move a finger digit 130. The power supply 180 can include a battery. For example, a battery of the power supply 180 can include one or more battery cells arranged in series or parallel, such as, but not limited to, 2, 4, 6, or 8 cells. Furthermore, in some cases, a battery of the power supply 180 can have a high-energy density. For example, a battery of the power supply 180 can include Lithium-ion (Li-ion), Lithium Polymer (Li-Pol), or the like. Specifications of the power supply 180 may vary across embodiments. For example, a power supply may be selected which fulfills power supply requirements of a motor 140 of the prosthesis 100. In some cases, the power supply 180 can have a nominal voltage between 5 V and 20 V, such as a nominal voltage of 7.4 V. However, the power supply 180 can be appropriately sized or rated based on power supply requirements of prosthesis 100.

The motor(s) 140 can be a brushed DC motor or a brushless motor. In some cases, the motor(s) 140 can be implemented as an electric rotary actuator. However, other types of motors or actuators may be used without departing from the spirit and scope of the description. In some cases, the motor(s) 140 can be controlled using pulse width modulation. For example, the controller 150 can supply or cause another component of the prosthesis 100 to supply a pulse width modulated signal to the motor(s) 140 to control movement of the finger digit(s) 130.

Rotation and Flexion Axes

Each finger digit 130 can include, or be in communication with, one or more motors 140. For example, a motor 140 can be configured to move at least a portion of the finger digit 130 about one or more axes.

Figure 2A:
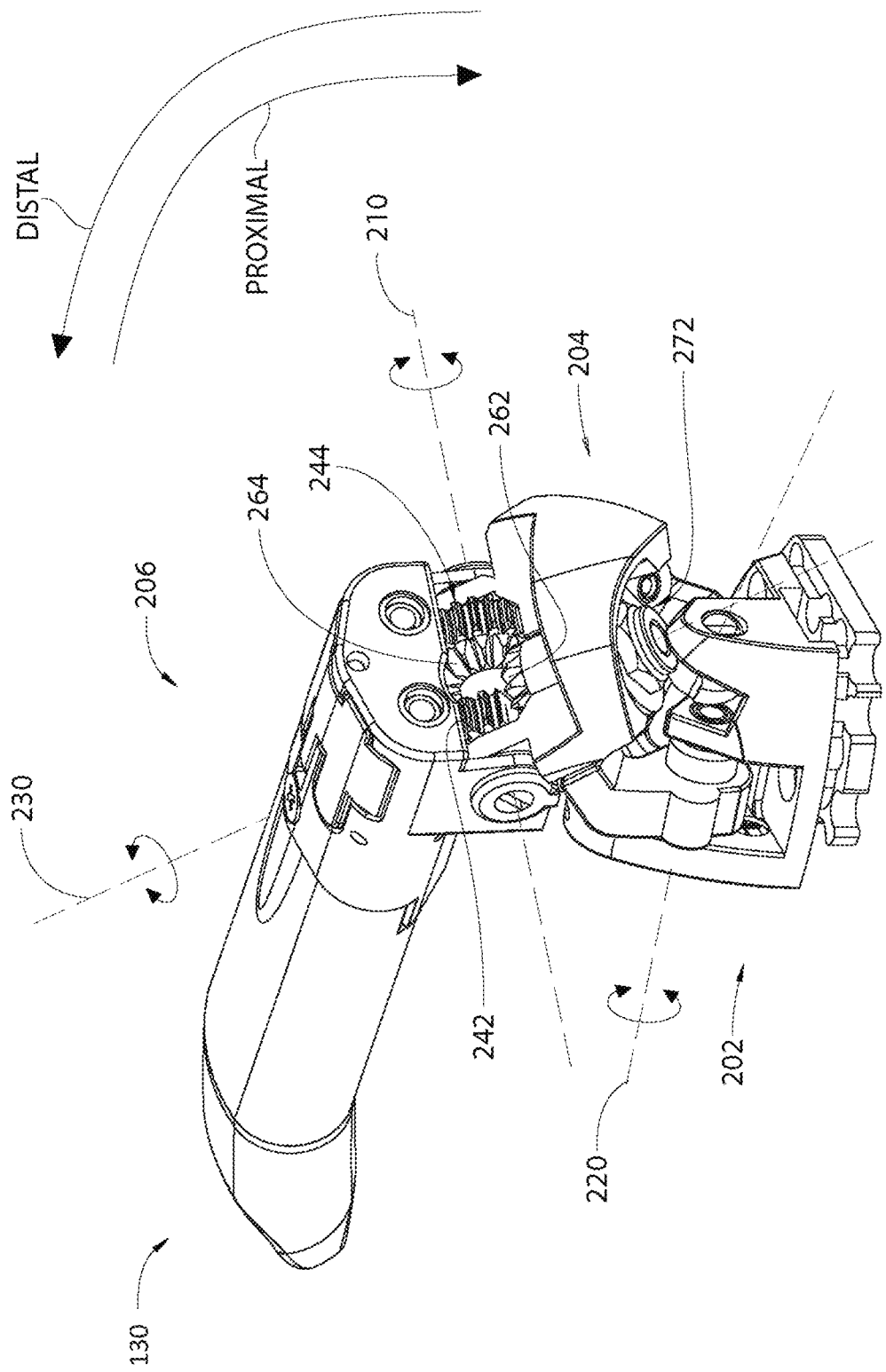
FIG. 2A is a perspective view of an example finger digit.

FIG. 2A is a perspective view of an example finger digit 130. In the illustrated example of FIG. 2A, the finger digit 130 is a thumb and includes a lower assembly 202, a middle assembly 204, and an upper assembly 206. As described herein, a motor 140 can cause the upper assembly 206 to rotate about one or more of various axes relative to the lower assembly 202. For example, the motor 140 can cause the upper assembly 206 to rotate about a flexion axis 210 (sometimes referred to as a pinch axis). As another example, the motor 140 can cause the upper assembly 206 to rotate about a rotation axis 220 (sometimes referred to as a lateral axis).

The flexion axis 210 may be defined and be fixed with respect to portions of the upper assembly 206. Further, the upper assembly 206 may move in directions other than merely rotating about the flexion axis 210. Thus, the orientation of the flexion axis 210 may also change, for example relative to the lower assembly 202, due to movement of the upper assembly 206. The upper assembly may rotate about the flexion axis 210 due at least in part to mechanical communication between various worm gears and worm wheels, as further described below.

The rotation axis 220 may be defined and be fixed with respect to portions of the lower assembly 202. The upper assembly 206 may move in directions other than merely rotating about the flexion axis 210. Thus, the orientation of the flexion axis 210 may change, for example relative to the lower assembly 202, due to movement of the upper assembly 206. The upper assembly 206 may rotate about flexion axis 210, about the rotation axis 220, or about the flexion axis 210 and the rotation axis 220 simultaneously. The upper assembly 206 may rotate about the rotation axis 220 due at least part to mechanical communication between worm gears, worm wheels, and bevel gears, as further described below.

Figure 2B:
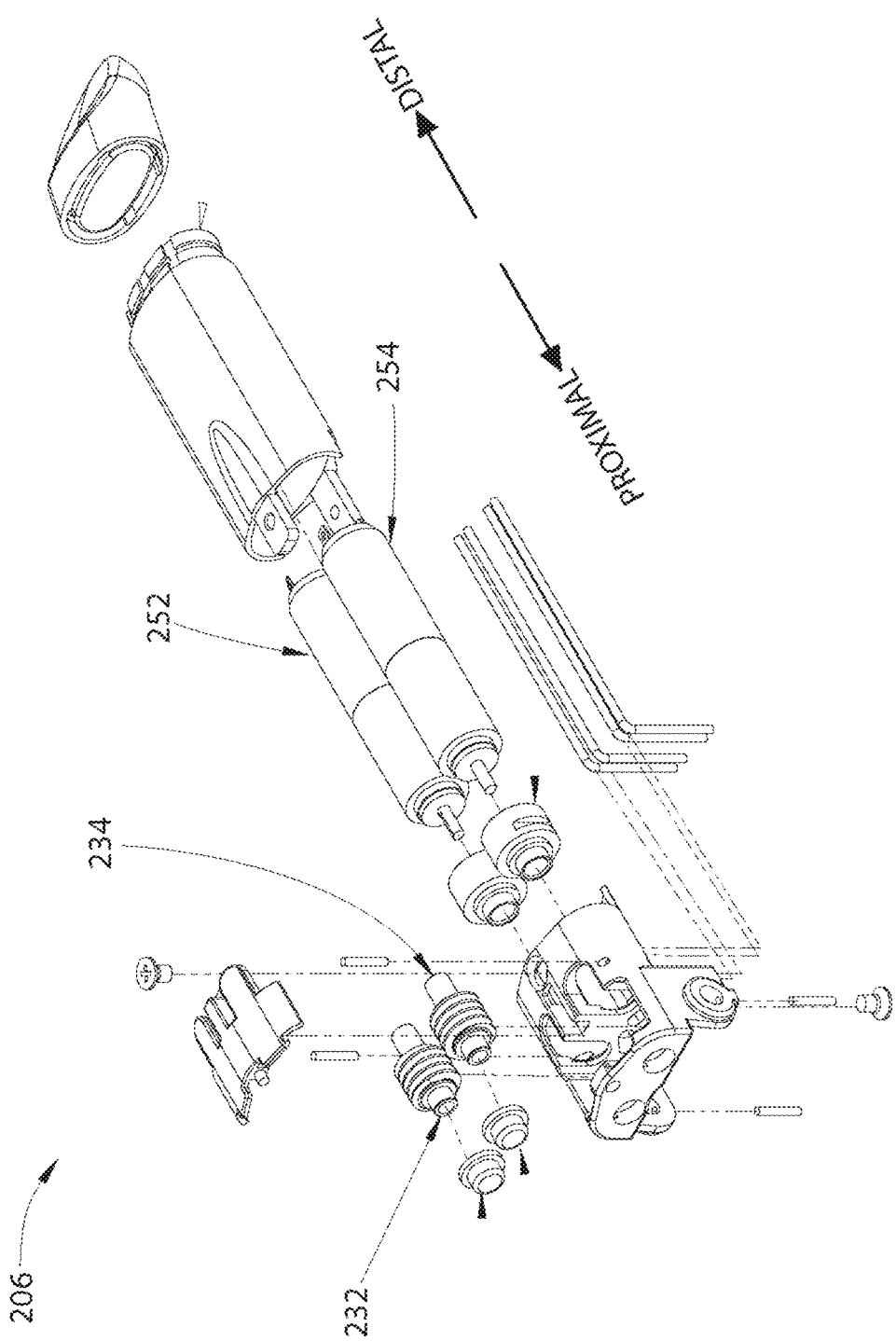
FIG. 2B is an exploded view of a portion of the upper assembly of the finger digit of FIG. 2A

FIG. 2B is an exploded view of a portion of the upper assembly 206 of the finger digit 130 of FIG. 2A. As shown by the combination of FIGS. 2A and 2B, the upper assembly 206 can include a first worm gear 232, a second worm gear 234, a first bevel gear 262, and a second bevel gear 264. The worm gears 232, 234 may be rotated by motor(s) 140, such as the first actuator 252 or the second actuator 254, as further described.

As shown by the combination of both FIGS. 2A and 2B, the worm gears 232, 234 mechanically communicate with the worm wheels 242, 244, respectively, of the middle assembly 204. Mechanical communication of the worm gear 232 with the worm wheels 242 can cause the upper assembly 206 to rotate about the flexion axis 210. Mechanical communication of the worm gear 234 with the worm wheels 244 can cause the upper assembly 206 to rotate about the rotation axis 220.

Actuation of the first actuator 252 can cause rotation of the upper assembly 206 about the flexion axis 210. For example, the first actuator 252 can cause the first worm gear 232 to rotate, and mechanical communication between a rotating first worm gear 232 and the first worm wheel 242 can cause the rotation of the upper assembly 206 about the flexion axis 210. That is, rotation of the first worm gear 232 can cause interaction with the first worm wheel 242. Interaction of gear teeth of the first worm gear 232 with the complementary projections of the first worm wheel 242 cause the first worm gear 232 to advance along the outer circumference of the first worm wheel 242. Advancement of the worm gear along the wheel 242 can cause the upper assembly 206 to rotate in a flexion-open or a flexion-closed direction about the flexion axis 210, depending on the direction of rotation of the worm gear 232. By "flexion-open", it is meant that the upper assembly 206 moves in a direction associated with extension of the finger digit 130. For example, the upper assembly 206 moves in a flexion-open direction or has a flexion-open motion when the upper assembly 206 rotates away from a palm of the hand 120. By "flexion-closed", it is meant that the upper assembly 206 moves in a direction associated with flexion of the finger digit 130. For example, the upper assembly 206 moves in a flexion-closed direction or has a flexion-closed motion when the upper assembly 206 rotates toward a palm of the hand 120.

Mechanical communication between the second actuator 254, the second worm gear 234, the second worm wheel 244, and bevel gears 262, 264 allows the upper assembly 206 to rotate about the rotation axis 220. For example, actuation of the second actuator 254 can cause rotation of the second worm gear 234. The second worm gear 234 includes a series of teeth that interact with a series of projections on the worm wheel 244. Accordingly, rotation of the second worm gear 234 causes rotation of the second worm wheel 244. Because the worm wheel 244 is rotationally fixed with the bevel gear 264, the bevel gear 264 will also rotate and thereby act against the bevel gear 262, which causes the upper assembly 206 to rotate about the rotation axis 220. Advancement of the worm gear along the wheel 244 causes the upper assembly 206 to rotate in a rotation-lateral or a rotation-palmar direction about the rotation axis 220, depending on the direction of rotation of the worm gear 234. By "rotation-lateral", it is meant that the upper assembly 206 moves in a direction associated with turning away from a palm of the hand 120. For example, the upper assembly 206 moves in a rotation-lateral direction or has a rotation-lateral motion when the upper assembly 206 rotates away from a palm of the hand 120. By "rotation-palmar," it is meant that the upper assembly 206 moves in a direction associated with turning towards a palm of the hand 120. For example, the upper assembly 206 moves in a rotation-palmar direction or has a rotation-palmar motion when the upper assembly 206 rotates toward a palm of the hand 120.

The first and second actuators 252, 254 can be actuated at distinct time intervals such that the upper assembly 206 rotates about one of the flexion axis 210 or the rotation axis 220. Alternatively, the first and second actuators 252, 254 can be actuated at overlapping time intervals, such that the upper assembly 206 can concurrently rotate about both the flexion axis 210 and the rotation axis 220. In some cases, actuation of the first actuator 252 or second actuator 254 may contribute to about one or both the flexion axis 210 and the rotation axis 220.

Although FIGS. 2A and 2B illustrates the finger digit 130 as a thumb, it will be understood that a finger digit 130 can include any of an index finger, a middle finger, a ring finger, or a pinky finger, or a thumb, and any of which may include the same or similar features or functionalities as shown or described with respect to FIGS. 2A and 2B. For example, any finger digit 130 can include or be in communication with a motor 140, and the motor 140 can move at least a portion of the finger digit 130 about one or more axes, such as a flexion axis 210 and/or the rotation axis 220. Furthermore, other rotations or movements may also be performed by a finger digit 130. For example, the finger digit 130 can include other joints along the upper assembly 206 that rotate or move as well.

In some cases, the prosthesis 100 can include a clutch assembly to allow for manual rotation of the upper assembly 206 about the rotation axis 220, for example to prevent damage in case of excessive force applied to the finger digit 130. Additional description and examples of the finger digit 130, such as a thumb, can be found in the '556 application, which was previously incorporated by reference.

Acceleration Profile

The controller 150 can implement an acceleration profile. Implementation of an acceleration profile can advantageously allow the controller 150 to reduce or control an amount of power consumed by a motor 140. In additional or alternatively, implementation of an acceleration profile can advantageously allow the controller 150 to reduce or control an amount of electrical or mechanical noise produced by the motor 140. For example, implementation of an acceleration profile can reduce an amount of power consumed and/or electrical or mechanical noise produced by the motor 140 as the motor 140 accelerates (e.g., as the motor 140 transitions from an idle state, or near-idle state, to a non-idle state). In some cases, the motor 140 is at an idle state when the motor 140 has a duty cycle of 0%, and the motor 140 is at a non-idle state when the motor 140 has a duty cycle above 0%.

Prior efforts of controlling a motor of a prosthetic hand include initializing the motor to a predetermined duty cycle level (sometimes referred to herein to as the "operating duty cycle"). Such an initialization generally includes a binary approach, where the duty cycle of the motor is directly transitioned from an idle state duty cycle (e.g., 0%) to the operating duty cycle, without a duty-cycle ramp-up in between. As a non-limiting example, if the operating duty cycle were a 100% duty cycle, prior efforts would initialize the motor 140 to run at 100% duty cycle, rather than progressively ramping the duty cycle, such as to some smaller duty cycle between 0% duty cycle and 100% duty cycle. This method of initializing the motor to the operating duty cycle advantageously allows the motor to achieve a desired speed or perform a desired movement as quickly as possible. Notably, however, initializing the motor 140 to the operating duty cycle can introduce electrical and/or mechanical noise into the prosthesis 100, as well as cause the motor to consume a sizable amount of energy from the power supply 180 of the prosthesis 100.

Conversely, by systematically or progressively increasing the duty cycle of the motor 140 to the operating duty cycle over a predetermined duration of time, the motor 140 can consume less energy from the power supply 180. Furthermore, in some instances, the difference in timing between a prosthesis that initializes the motor to the operating duty cycle and a prosthesis 100 that implements the disclosed acceleration profile is not noticeable to human eye. In some cases, the controller 150 can implement an acceleration profile on multiple motors 140 concurrently or sequentially.

The elements outlined for routine 300 can be implemented by one or more computing devices that are associated with the prosthesis 100, such as the controller 150. Accordingly, routine 300 has been logically associated as being generally performed by the controller 150. However, the following illustrative example should not be construed as limiting.

At block 302, the controller 150 determines to move the finger digit 130. In some cases, the controller 150 determines to move the finger digit 130 to a new or different position, such as from first position to a second position.

The determination to move the finger digit 130 can be based at least in part on one or more activation signals. For example, the prosthesis 100 can include or be in communication with one or more user input devices 190, such as one or more of a myoelectric electrode, a pressure sensitive resistor, a neural implant, a mechanical switch, or the like. The controller 150 can continuously or periodically monitor the user input device(s) 190 or can receive signals from the user input device(s) 190. For example, a myoelectric electrode can detect electric activity from a muscle of a wearer of the prosthesis 100, and the myoelectric electrode can relay that information to the controller 150.

In some cases, based at least in part on the information from the user input device(s) 190, the controller 150 can determine to move the prosthetic finger. For example, signals received from the user input device(s) 190 can be activation or instruction signals. Responsive to the controller 150 detecting an activation or an instruction signal, the controller 150 can determine to move the prosthetic finger 130. In some cases, the data store 170 stores an operating profile that includes prosthetic finger manipulation data, such as hand grip identifiers, motor identifies, direction identifiers, or the like, and a plurality of activation or instruction signal identifiers. The operating profile can associate the prosthetic finger manipulation data with the each of the activation or instruction signal identifiers such that the controller 150 can determine to move the finger digit 130, identify a motor, or identify a direction to move the finger digit 130 based at least in part on signals received from the user input device(s) 190.

The determination to move the finger digit 130 can be based at least in part on one or more stored computer executable instructions. For example, the data store 170 can store computer executable instructions that, when executed by the controller 150, cause the controller 150 to determine to move the finger digit 130, identify a motor, or identify a direction to move the finger digit 130.

In some cases, as part of the determination to move the finger digit 130, the controller 150 can select or identify motor(s) 140 to operate in order to achieve a desired movement. For example, the controller 150 controller can select or identify the motor(s) 140 associated with the finger digit 130. In some cases, the selection or identification of the motor(s) 140 is based at least in part on the desired movement, such as a selected hand gesture, a selected hand grip, or the like. In some cases, the data store 170 stores an operating profile that includes a plurality of hand gestures or hand grips and an indication of the motor(s) 140 corresponding to each of the plurality hand gestures or hand grips. The operating profile can associate each of the plurality hand gestures or hand grips with the corresponding motor(s) 140 such that the controller can identify or select the motor(s) 140 from the operating profile based at least in part on a desired hand gesture or hand grip.

In some cases, as part of the determination the move the finger digit 130, the controller 150 can identify the direction in which a motor 140 is to move the finger digit 130. For example, the controller 150 can identify the flexion-open direction or the flexion-close direction, as described herein. As another example, the controller 150 can identify the rotation-palmar direction or the rotation-lateral direction, as described herein.

At block 304, the controller 150 communicates a first command signal. The communication of the first command signal can be based at least in part on the determination to move the finger digit 130 at block 302. In some cases, first command signal is a pulse width modulation (PWM) signal to the motor 140. In some cases, the first command signal causes a PWM signal to be transmitted to the motor 140.

Prior to the communication of the first command signal, the motor 140 can be in an idle state. That is, the motor 140 can have a duty cycle equal to an idle state duty cycle. The idle state duty cycle can vary across embodiments. In some instances, the idle state duty cycle can correspond to a 0% duty cycle, which can be equivalent to the motor 140 drawing no or nominal power from the power supply 180.

In some cases, the idle state duty cycle can correspond to a higher than zero value, such as a duty cycle value that is low enough so as to not overcome starting friction (sometimes referred to as static friction or stiction) associated with the components of the motor 140. For example, generally an electric motor 140 does not operate (that is, a shaft of the electric motor 140 does not rotate) until power is applied to the electric motor 140. In some cases, even when power is applied (such that the duty cycle of the motor is a non-zero duty cycle), the motor 140 can remain unmoved due to stiction of the motor 140. In some cases, the idle state duty cycle can correspond to a duty cycle of the motor 140 that is not large enough to overcome the stiction of the motor 140. For example, the idle state duty cycle can be 0%, 1%, 5%, 10%, 15%, 20%, less than 1%, less than 5%, less than 10%, or less than 20%. It will be understood that the idle state duty cycle can be various other duty cycle values as well.

The first command signal can cause a duty cycle of the motor 140 to increase from the idle state duty cycle to satisfy a first duty cycle level. The first duty cycle level can be a duty cycle that is greater than the idle state duty cycle, but less than a second duty cycle level, described herein. In some cases, the first duty cycle level can correspond to the minimum duty cycle of the motor 140 that will allow the motor 140 to overcome the stiction of the motor 140. In certain cases, the first duty cycle level can correspond to a duty cycle that is higher than the minimum duty cycle of the motor 140 that will allow the motor 140 to overcome the stiction of the motor 140. For example, to ensure that the motor 140 will overcome the stiction of the motor 140, the first duty cycle level can correspond to a predetermined value or percentage higher than the minimum duty cycle of the motor 140 that will allow the motor 140 to overcome the stiction of the motor 140. For example, the first duty cycle level can be 1, 2, 3, 4, 5, 6, 7, 8, 9, or 10% more duty cycle than the minimum duty cycle of the motor 140 that will allow the motor 140 to overcome the stiction of the motor 140. It will be understood that the first duty cycle level can be various other duty cycle values as well.

In some cases, the first command signal can cause the motor 140 to initialize directly to the first duty cycle level, such that the motor 140 is transitioned from the idle state duty cycle to the first duty cycle level without a gradual ramp-up period.

At block 306, the controller 150 communicates a second command signal. The controller 150 can communicate the second command signal after or concurrently with the communication of the first command signal at block 304. In some cases, the second command signal can cause a systematic increase in the duty cycle of the motor 140 from the first duty cycle level to a second duty cycle level. In certain cases, the second duty cycle level can correspond to an operating duty cycle level, or the duty cycle at which the motor 140 typically operates for the duration of the movement or for a substantial portion of the movement.

The systematic increase in the duty cycle can include a gradual or controlled increase in the duty cycle from the first duty cycle level to the second duty cycle level. In some cases, the systematic increase can be a uniform increase from the first duty cycle level to the second duty cycle level. In certain cases, the systematic increase can be a non-uniform increase from the first duty cycle level to the second duty cycle level. In some cases, the systematic increase includes a stepwise increase. For example, the duty cycle of the motor can be increase in a stepwise pattern from the first duty cycle level to the second duty cycle level, for example, including 5, 8, 10, 12, 15, or 20 "steps" or discrete points in the stepwise pattern. In some cases, the systematic increase, such as the stepwise pattern, corresponds to a simple exponential curve, an S-shaped exponential curve, or a J-shaped exponential curve.

The systematic increase in the duty cycle of the motor 140 from the first duty cycle level to the second duty cycle level can occur over a predetermined duration of time. The length of the predetermined duration of time can vary across embodiments. For example, the length of the first predetermined duration of time can be 20, 40, 60, 80, 100, 120, or 140 ms (+/−5 to 10 ms). In some cases, the length of the predetermined duration of time can be between 40 to 160 ms, 60 to 140 ms, or 80 to 120 ms. It will be understood that various other durations can be utilized.

The systematic increase in the duty cycle of the motor 140 from the first duty cycle level to the second duty cycle level can advantageously allow the prosthesis 100 to conserve energy of the power supply 180 that might otherwise be consumed by the motor 140 if the motor 140 was initialized to the second duty cycle level. Furthermore, the length of time added to a particular movement of the prosthesis 100 by implementing an acceleration profile, as described herein, can be negligible. For example, in some cases, the addition of the acceleration profile can add less than 100 ms to a movement by the prosthesis 100, such as about 10 ms.

Figure 3:
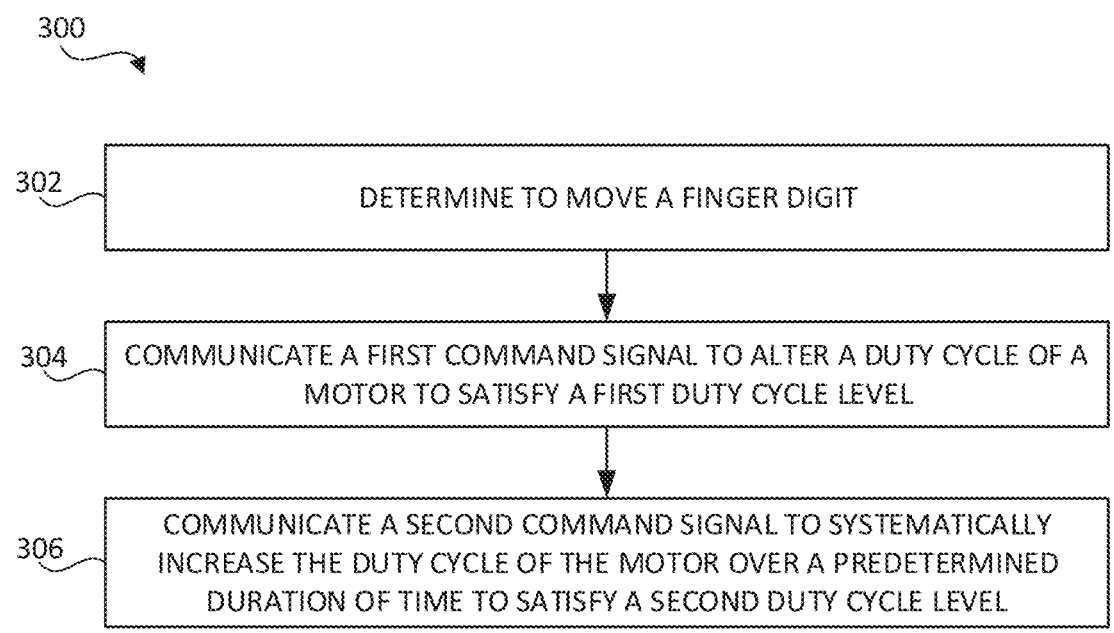
FIG. 3 is a flow diagram illustrative of a routine for an example acceleration profile implemented by a prosthesis on a motor that is configured to move a finger digit of the prosthesis.

It will be understood that the various blocks of FIG. 3 can be implemented in a variety of orders, and that the prosthesis 100 can implement one or more of the blocks concurrently and/or change the order, as desired. For example, the controller 150 can concurrently communicate the first and second command signals.

Furthermore, it will be understood that fewer, more, or different blocks can be used as part of the routine 300. For example, the routine 300 can include blocks for communicating another command signal to reduce a duty cycle of the motor. For example, the routine 300 can implement some or all of various blocks of FIGS. 5A, 5B, 9, or 10 in routines 500A, 500B, 900, or 1000 concurrently or change the order as desired. Furthermore, the routine 300 can omit certain blocks, such as, but not limited to, block 302. For example, in some cases, the controller 150 does not determine to move the finger digit 130.

Figure 4:
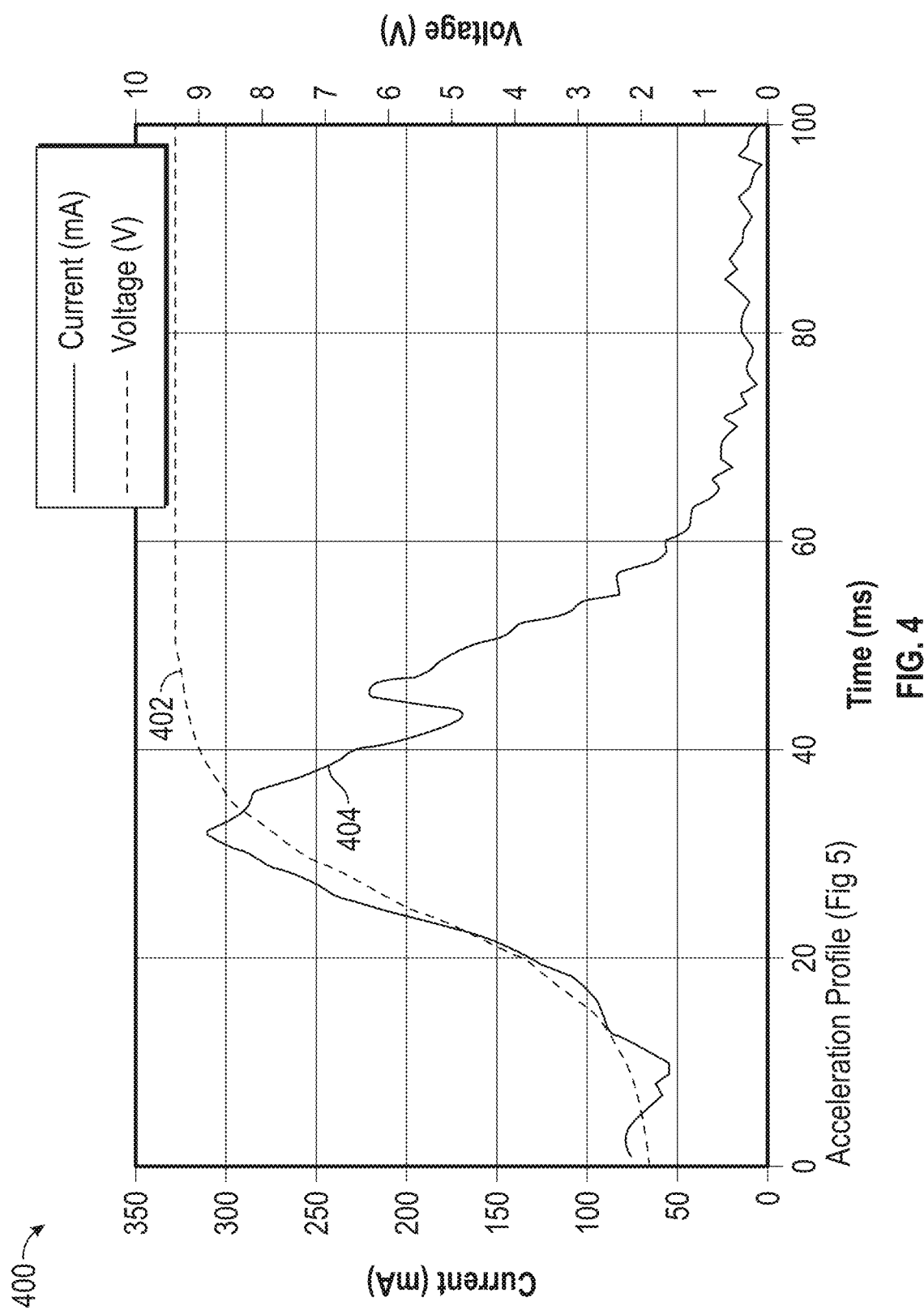
FIG. 4 is a graph illustrating an example drive profile for a motor that includes an example acceleration profile.

FIG. 4 is a graph 400 illustrating an example drive profile for a motor that includes an example acceleration profile. The horizontal axis on the graph 400 corresponds to time, in milliseconds (ms). For the voltage channel 402, the vertical axis on the graph 400 corresponds to a voltage, in volts (V), supplied to the motor. For the current channel 404, the vertical axis on the graph 400 corresponds to a current, in milliamps (mA), supplied to the motor. In the illustrated example, the acceleration profile has a duration of 100 ms, beginning a time=0 ms and ending to time=100 ms.

The graph 400 illustrates an example systematic increase of the duty cycle of the motor 140 over a 50 ms duration. With respect to the voltage channel 402, at the beginning of the drive profile (corresponding to time=0), rather than initializing the motor 140 to start at 100% duty cycle, the motor 140 is initialized to approximately a 20% duty cycle. This is shown by the voltage channel 402 having a value of about 1.88 V at time=0 (which is 20% of the 9.4 V value at 100% duty cycle). During the first 50 ms duration of the 100 ms acceleration profile, the voltage is systematically increased, such that the shape of the increase corresponds to an S-shaped exponential curve. In the illustrated example, the voltage is systematically increased by increasing the duty cycle every five ms, at least during the first 40 ms. The size of the duty cycle increase varies depending on the time. For example, the average duty cycle increase during the 20-50 ms range is larger than the average duty cycle increase during the 0-20 ms time range, which is larger than the average duty cycle increase during the 40-5 ms time range.

By varying the step size of the duty cycle increase, the controller is able to approximate an S-shaped exponential curve. With respect to the current channel 404, at about t=30 ms, the current spikes to approximately 310 mA (corresponding to the motor 140 overcoming a stiction of the motor 140) and then the current gradually reduces until about t=80, where the current remains approximately constant.

In some instances, a duration of the acceleration profile can be longer than a duration of the systematic voltage increase and/or a duration of the current spike and decrease. For example, in the illustrated example, the entire graph 400 corresponds to the acceleration profile, which has a duration of 100 ms. Furthermore, as described herein, the voltage is initialized to a 20% duty cycle and is increased to a 100% duty cycle over 50 ms. Furthermore, in the illustrated example, it takes about 80 ms for the current to spike to overcome the stiction and then subsequently reduce. In some cases, the controller 150 can ignore a motor-stall-threshold (described further here) during the duration of the acceleration profile (in this example, 100 ms). For instance, as illustrated in FIG. 4, during the acceleration profile, the motor 140 to draws a current that may satisfy a current threshold. However, to ensure that the initial current consumed to overcome a stiction of the motor 140 is not mistaken for a stall condition, the controller 150 can ignore the motor-stall-threshold during the duration of the acceleration profile.

Movement of a Finger Digit in a Rotation-Lateral, Rotation-Palmar, or Flexion-Open Direction As described herein, the motor(s) 140 can control movement of the finger digit 130. For example, a motor 140 can move the finger digit 130 in a flexion-open direction (corresponding to flexion of the finger digit 130) or a flexion-closed direction (corresponding to extension of the finger digit 130). As another example, the same or a different motor 140 can move the finger digit 130 in rotation-lateral direction (corresponding to an outward rotation of the finger digit 130) or a rotation-palmar direction (corresponding to an inward rotation of the finger digit 130). In some cases, two different motors 140 can move the finger digit 130 concurrently or in sequence. For example, one motor 140 can move the finger digit 130 in a flexion-open direction or a flexion-closed direction another motor 140 can move the finger digit 130 in a rotation-lateral direction or a rotation-palmar direction.

For each of the flexion-open, rotation-lateral, and rotation-palmar motions, rather than closing upon an object, the finger digit 130 is generally either opening or rotating. Therefore, during any of the flexion-open, rotation-lateral, and rotation-palmar motions, the finger digit 130 is expected to move unimpeded through the motion. That is, to complete the motion, the finger digit 130 is not expected to meet an object or an opposing force along its path, unless or until the finger digit 130 reaches its full range of motion or a mechanical end stop along the axis over which it is traveling.

In contrast, a wearer of the prosthesis 100 generally uses the flexion-closed motion to grasp an object or to pinch the finger digit 130 together with another finger digit 130. Therefore, in some cases, during the flexion-closed motion, the finger digit 130 is expected to meet an object or other opposing force along its path. Specifically, in certain cases, with respect to grasping an object, the finger digit 130 is expected to meet the object prior to the finger digit 130 reaching its full range of motion along the flexion axis.

Due to these differing expectations of the flexion-open, rotation-lateral, and rotation-palmar motions versus the flexion-closed motion, in some cases, the controller 150 can operate a motor 140 differently, depending on its movement. For example, if the finger digit 130 meets an object or other opposing force along its path during any of the flexion-open, rotation-lateral, or rotation-palmar motions, the controller 150 can cause the motor 140 to stop moving the finger digit 130, either immediately or shortly thereafter. By causing the motor 140 to stop moving the finger digit 130, the prosthesis 100 can conserve energy of the prosthesis 100. For example, energy consumption can be reduced because the motor 140 does not consume, or consume less, energy once the finger digit 130 meets an object in its path.

As another example, if the finger digit 130 meets an object or other opposing force along its path during the flexion-closed motion, the controller 150 can cause the motor 140 to continue moving the finger digit 130 along the flexion axis, at least for a predetermined duration of time. By continuing to move the finger digit 130 along the flexion axis, the controller 150 can cause the finger digit 130 to increase the force, such as a pinch force, exerted on the object, which can secure a grip on the object. Furthermore, in some cases, after the motor 140 continues to move the finger digit 130 along the flexion axis for the predetermined duration of time, the controller 150 can, for a second time, cause the motor 140 to move the finger digit 130 along the flexion axis towards the object, so that the finger digit 130 can further increase the force exerted on the object. In some cases, to move the finger digit 130 for the second time, the controller 150 can drive the motor 140 using a pulsing regime to allow the finger digit 130 to further increase the force exerted on the object.

Figure 5A:
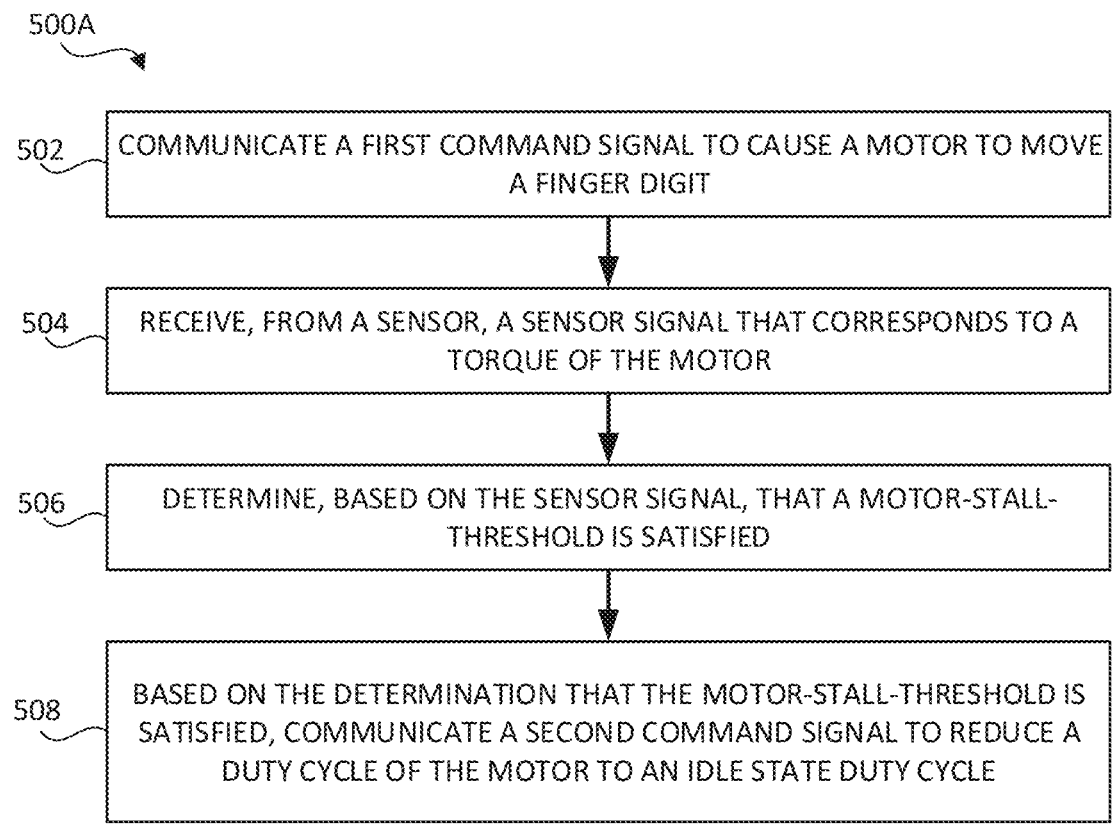
FIG. 5A is a flow diagram illustrative of an example routine of a prosthesis.

FIG. 5A is a flow diagram illustrative of an example routine 500 of a prosthesis 100. The elements outlined for routine 500 can be implemented by one or more computing devices that are associated with the prosthesis 100, such as the controller 150. Accordingly, routine 500 has been logically associated as being generally performed by the controller 150, but the following illustrative example should not be construed as limiting.

At block 502, the controller 150 communicates a first command signal to the motor 140 to move the finger digit 130. The first command signal can initiate an acceleration profile, as described herein at least with respect to FIG. 3. In some cases, the first command signal causes the motor 140 to move the finger digit 130 in a flexion-open, rotation-lateral, or rotation-palmar motion. In some cases, the first command signal causes the motor 140 to move the finger digit 130 in a flexion-closed motion. In some cases, the first command signals varies the duty cycle of the motor 140 in proportion to one or more input signals received from an input device(s) 190.

Prior to receiving the first command signal, the motor 140 can be in an idle state, as described herein. Alternatively, prior to receiving the first command signal, the motor 140 can be in a non-idle state. For example, in some cases, prior to receiving the first command signal, the motor 140 can be moving the finger digit 130 in one or more of a flexion-open, rotation-lateral, rotation-palmar, or flexion-closed motion. In some cases, the first command signal causes the motor 140 to change its direction or motion, or the first command signal can increase or decrease a duty cycle of the motor 140.

At block 504, the controller 150 receives a sensor signal from a sensor(s) 160 that corresponds to a torque of the motor 140. As described herein, the sensor(s) 160 can be on or more of various sensors including, but not limited to, one or more torque sensors, current sensors, voltage sensors, force sensors, acceleration or orientation sensors, or position sensors. The sensor signal can correspond to or be usable to determine one or more of a torque of the motor 140, a speed of the motor 140, a turning force of the motor 140, a voltage drawn by the motor 140, a current drawn by the motor 140, a force again the finger digit 130, a position of the finger digit 130, or the like.

At block 506, the controller 150 determines, based at least in part on the sensor signal, that a motor-stall-threshold is satisfied. In some cases, the motor-stall-threshold corresponds to a stalling of the motor 140, such as when the motor 140 stops rotating or slows in rotation due to a load torque being greater than a shaft torque of the motor 140. During a stalling of the motor 140, the motor 140 may draw additional current but motor 140 may not rotate, or may rotate more slowly. In some cases, the motor-stall-threshold corresponds to the finger digit 130 having come in contact with an object or other opposing force along its path of motion.

The motor-stall-threshold can be satisfied in various ways. For example, to determine whether the motor-stall-threshold is satisfied, the controller 150 can compare a value associated with the sensor signal to one or more thresholds. For example, in some cases, the motor-stall-threshold can be satisfied if any one or more of a torque of the motor 140 satisfies a torque threshold, a current drawn by the motor 140 satisfies a current threshold, a voltage drawn by the motor 140 satisfies a voltage threshold, or a force on the finger digit 130 satisfies a force threshold.

In some cases, the motor-stall-threshold can be satisfied based at least in part on a determination that a torque of the motor 140 satisfies a torque threshold. As an example, if the torque of the motor 140 falls below the torque threshold, the torque threshold can be satisfied. The torque threshold can vary depending on characteristics of the motor 140, design constraints, or the like. In some cases, the torque threshold is equal to 0 newton-meters (N·m) or some other torque.

In some cases, the motor-stall-threshold can be satisfied based at least in part on a determination that a current drawn by the motor 140 from a power source satisfies a current threshold. As an example, if the current drawn by the motor 140 exceeds the current threshold, the current threshold can be satisfied. The current threshold can vary depending on characteristics of the motor 140, design constraints, or the like. In some cases, the current threshold is equal to between 100-900 mA, or is some other current.

In some cases, the motor-stall-threshold can be satisfied based at least in part on a determination that a force on the finger digit 130 satisfies a force threshold. For example, the finger digit 130 can include one or more force sensors, such as capacitive or inductive force sensors. If the force on the finger digit 130 exceeds the force threshold, the force threshold can be satisfied. The force threshold can vary across embodiments. For example, the force threshold can be equal to between 5 and 15 N, or some other force.

In some cases, the motor-stall-threshold can be satisfied based at least in part on a determination that a speed of the motor 140, or a speed of the finger digit 130, satisfies a speed threshold. For example, motor speed, for example in revolutions per minute (RPM), can be determined based on sensor data, such as data from an optical encoder positioned on the motor 140. In some cases, if the speed of the motor 140 falls below the speed threshold, the speed threshold can be satisfied. The speed threshold can vary across embodiments. As another example, speed of the finger digit 130 can be determined based on sensor data, such as data from an absolute position sensor placed on the finger digit 130. In some cases, if the speed of the finger digit 130 falls below the speed threshold, the speed threshold can be satisfied. The speed threshold can vary across embodiments.

In some cases, the routine 500 can include any one or any combination of blocks 508, 510, and/or 512. In some cases, if the first command signal causes the motor 140 to move the finger digit 130 in any of a rotation-lateral, rotation-palmar, flexion-open direction, then the routine 500 can include block 508. In some cases, if the first command signal causes the motor 140 to move the finger digit 130 in a flexion-closed direction, then the routine 500 can include any one of blocks 510, 512, or 514. However, it will be understood that the routine 500 can include any one of blocks 510, 512, or 514, regardless of the direction (e.g., rotation-lateral, rotation-palmar, flexion-open, or flexion-closed) in which the first command signal causes the motor 140 to move.

At block 508, based at least in part on the determination that the motor-stall-threshold is satisfied, the controller 150 communicates a second command signal to the motor 140 to reduce the duty cycle of the motor 140 to the idle state duty cycle, and the motor 140 returns to an idle state. In some cases, the reduction of the duty cycle of the motor 140 is instantaneous or close to instantaneous. For example, the reduction of the duty cycle of the motor 140 to the idle state duty cycle can occur over a duration of less than 5, 10, 15, 20, 25, or 30 ms, or some other duration, from the time at which the controller determines the motor-stall-threshold is satisfied. In some cases, the second command signal can correspond to a removal of the supply of voltage to the motor 140.

It will be understood that fewer, more, or different blocks can be used as part of the routine 500A. For example, in some cases, at block 506, the controller 150 determines that the motor-stall-threshold is not satisfied. For example, the controller 150 can determine that the torque does not satisfy the torque threshold, the current drawn by the motor does not satisfy the current threshold, the voltage by the motor does not satisfy the voltage threshold, or the force on the finger digit 130 does not satisfy the force threshold. In some cases, any one or more of these conditions will cause the motor-stall-threshold to not be satisfied. In some cases, the motor-stall-threshold will not be satisfied when all of these conditions are not satisfied. If the motor-stall-threshold is not satisfied, the controller 150 can end the routine 500A. Alternatively, the controller 150 can return to block 504. For example, the controller 150 can periodically or continuously receive sensor signals from the sensor(s) 160 or input device(s) 190, can compare values associated with the sensor signals to the one or more threshold to determine whether the motor-stall-threshold is satisfied.

Furthermore, the blocks of FIG. 5A can be implemented in a variety of orders, and that the prosthesis 100 can implement one or more of the blocks concurrently and/or change the order, as desired. Furthermore, fewer, more, or different blocks can be used as part of the routine 500A. For example, in some cases, rather than reducing the duty cycle of the motor 140 to an idle state duty cycle based on a determination that the motor-stall-threshold is satisfied, the controller 150 can communicate a command signal to reduce the duty cycle until the motor-stall-threshold is no longer satisfied. For example, the desired force of the finger digit 130 may be determined or set based at least in part on a strength of an input signal received from an input device(s) 190. In some cases, the controller 150 can communicate a command signal to control the duty cycle of the motor 140 to achieve this desired force. However, based at least in part on a satisfaction of a motor-stall-threshold, the controller 150 can communicate a command signal to reduce the duty cycle of the motor 140, thereby reducing the current consumption such that the motor-stall-threshold is no longer satisfied. The controller 150 can continue to drive the motor 140 at this reduced duty cycle for a duration of time.

Furthermore, the routine 500A can implement some or all of various blocks of FIGS. 3, 5B, 9, or 10 in routines 300, 500B, 900, or 1000 concurrently or change the order as desired. Furthermore, the routine 500A can omit certain blocks, such as, but not limited to, block 508. Although routine 500A is generally described with respect to moving a finger digit 130 in a rotation-lateral, rotation-palmar, or flexion-open direction, it will be understood that the routine 500A can be implemented for any movement of the finger digit 130, regardless of the direction (e.g., rotation-lateral, rotation-palmar, flexion-open, or flexion-closed) in which the first command signal causes the motor 140 to move.

Furthermore, in some cases, two motors 140 can be associated with the same finger digit 130. For example, a first motor can move a finger digit 130 in a rotation movement (e.g., any of the rotation-lateral or rotation-palmar directions), while a second motor 140 can move the finger digit 130 in a flexion movement (e.g., in any of the flexion-open or flexion-closed directions). In some cases, each of the first and second motor 140 can concurrently execute routine 500A to cause concurrent rotation and flexion movement of the finger digit 130.

Figure 6:
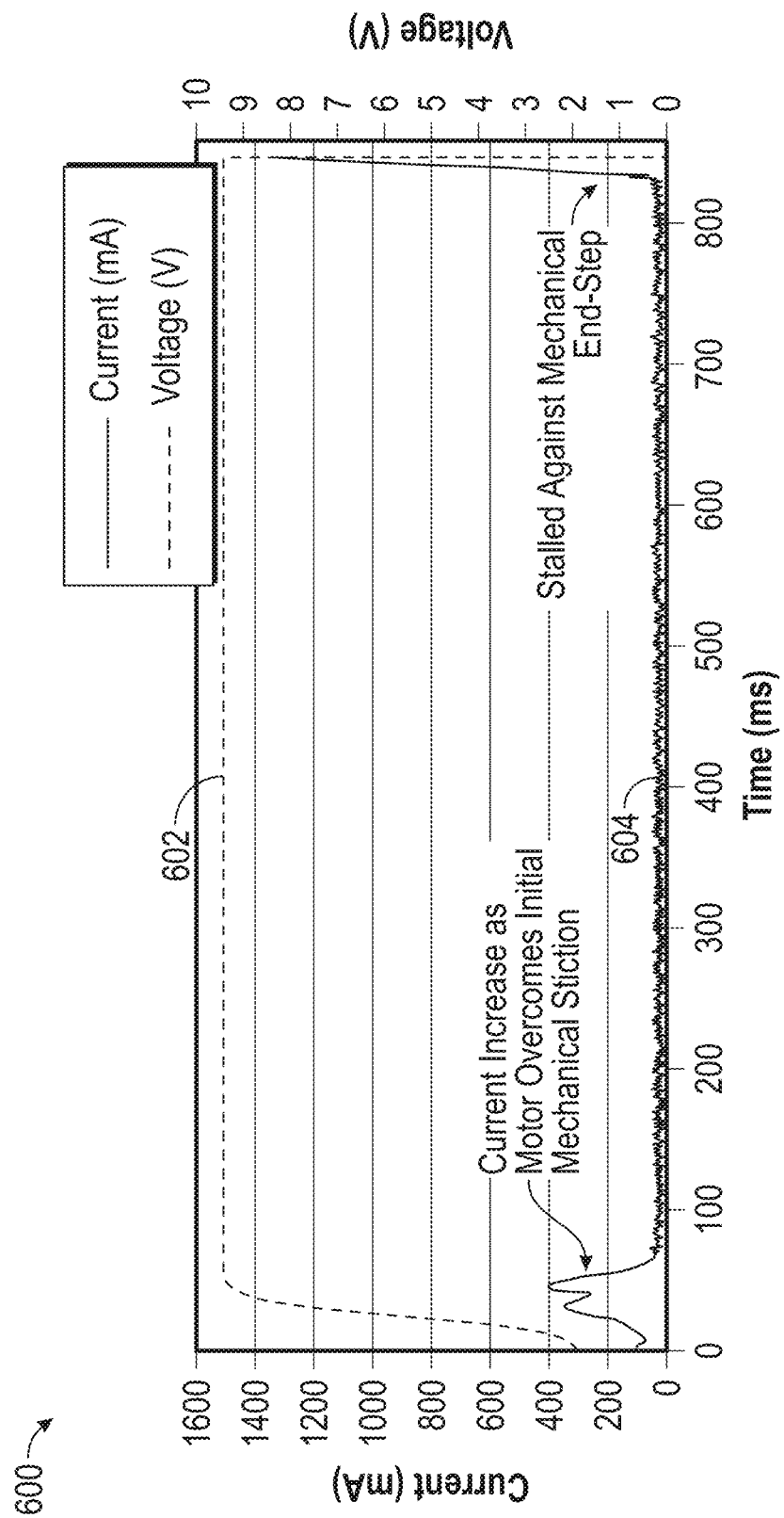
FIG. 6 is a graph illustrating an example drive profile for a motor.

FIG. 6 is a graph 600 illustrating an example drive profile for a motor 140. The horizontal axis on the graph 600 corresponds to time, in ms. For the voltage channel 602, the vertical axis on the graph 600 corresponds to a voltage (V), in volts, supplied to the motor 140. For the current channel 604, the vertical axis on the graph 600 corresponds to a current, in mA, drawn by the motor 140. In some cases, the graph 600 corresponds to the motor 140 moving a finger digit 130 in any of the rotation-lateral, rotation-palmar, or flexion-open directions. In the illustrated example of graph 600, prior to time=0, the motor 140 resides in an idle state, having an idle state duty cycle.

With respect to the voltage channel 602, at the beginning of the drive profile, which corresponds to time=0, rather than initializing the motor 140 to start at 100% duty cycle, the motor 140 to initialized to start at a 20% duty cycle. This is shown by the voltage channel 602 having a value of 1.88 V at time=0 (which is 20% of the 9.4 V value at 100% duty cycle). Over the first 50 ms, the finger digit 130 is accelerated by systematically increasing the voltage supplied to the motor 140 until the motor 140 reaches 100% duty cycle. The motor 140 continues to operate at 100% duty cycle until a motor-stall-threshold is satisfied, indicating that movement of the finger digit 130 is stalled against a mechanical end stop of the prosthesis 100. Based at least in part on the motor-stall-threshold being satisfied, the controller 150 causes the duty cycle of the motor 140 to be reduced to the idle state duty cycle, which includes reducing the voltage. In some instances, during the acceleration profile, which in this example has a duration of 100 ms, the motor-stall-threshold may be satisfied. For example, the acceleration profile may cause the motor to draw a current that satisfies a current threshold. However, in some cases, during the duration of the acceleration profile, the controller 150 can ignore the motor-stall-threshold and allow the motor 140 to draw sufficient current to accelerate according to an acceleration profile.

With respect to the current channel 604, the current increases to approximately 400 mA over the first 50 ms, which can correspond to the motor 140 overcoming a stiction of the motor 140. In the illustrated example, after the current reaches 400 mA (at approximately t=50 ms), it takes approximately 30 ms for the current consumption to drop to a residual level (e.g., lower than approximately 50 mA). In some cases, to ensure the initial current consumed to overcome a stiction of the motor 140 is not mistaken for a stall condition, the controller 150 can ignore the motor-stall-threshold and allow the motor 140 to draw sufficient current to accelerate according to an acceleration profile. After the acceleration profile ends, which in this example is after 100 ms, the controller 150 can continue to monitor the motor-stall-threshold. As described herein, the increase in current towards the end of the graph 600 corresponds to the finger digit 130 stalling against a mechanical end stop of the prosthesis 100. The current increases as the motor 140 draws motor current to develop a torque or counteract the opposing force of the mechanical end stop. As illustrated, in response to the motor-stall-threshold being satisfied (which, in this example, corresponds to the current satisfying a current threshold), the duty cycle of the motor 140 is reduced to the idle state duty cycle, which includes reducing the current.

Movement of a Finger Digit in a Flexion-Closed Direction

Figure 5B:
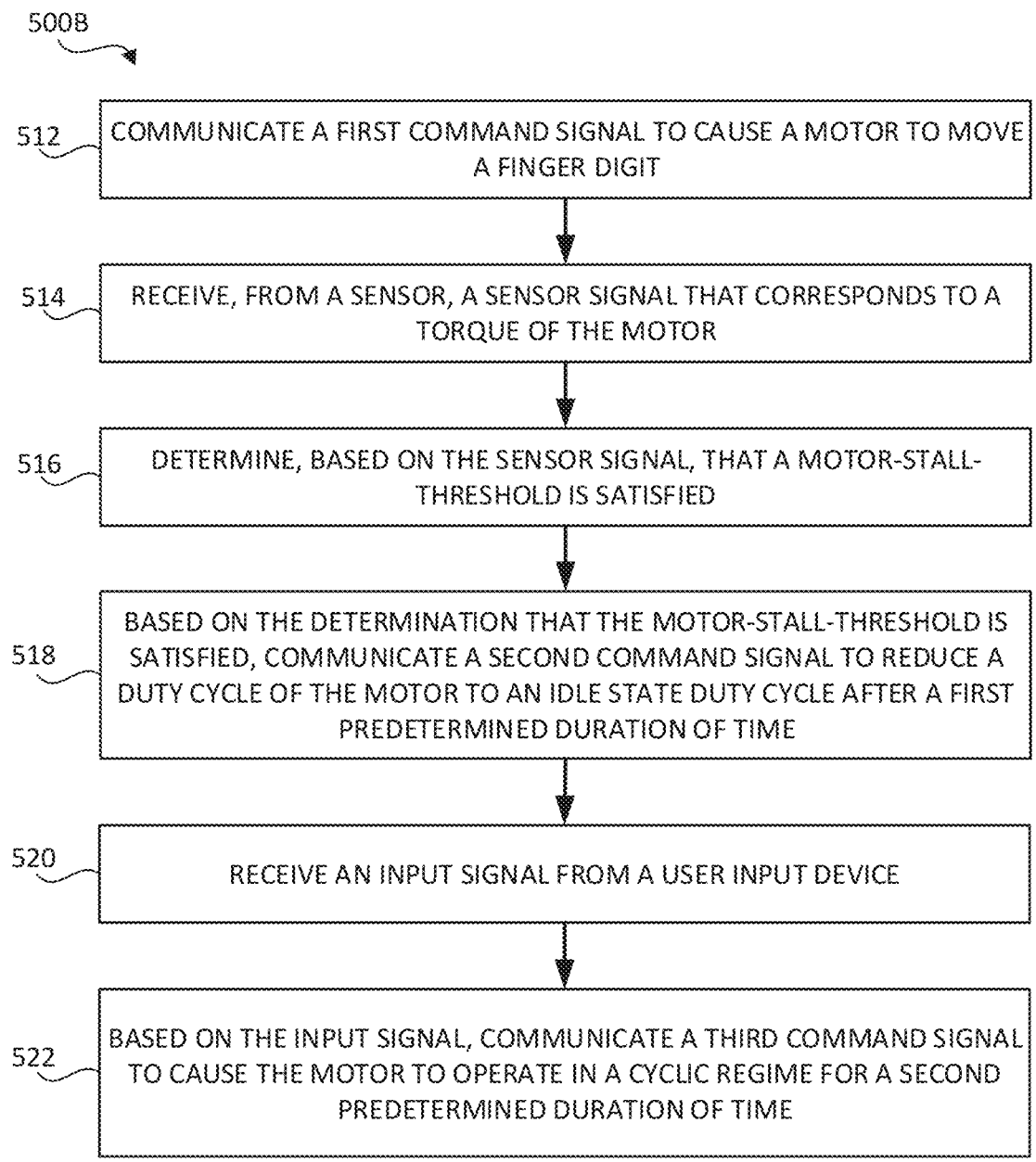
FIG. 5B is a flow diagram illustrative of an example routine of a prosthesis.

FIG. 5B is a flow diagram illustrative of an example routine 500B of a prosthesis 100. The elements outlined for routine 500B can be implemented by one or more computing devices that are associated with the prosthesis 100, such as the controller 150. Accordingly, routine 500B has been logically associated as being generally performed by the controller 150, but the following illustrative example should not be construed as limiting.

At block 512, similar to block 502 of FIG. 5A, the controller 150 communicates a first command signal to cause the motor 140 to move the finger digit 130.

At block 514, similar to block 504 of FIG. 5A, the controller 150 receives, from sensor(s) 160, a sensor signal that corresponds to a torque of the motor 140.

At block 516, similar to block 506 of FIG. 5A, the controller 150 determines, based at least in part on the sensor signal received at block 514, that a motor-stall-threshold is satisfied.

At block 518, based at least in part on the determination that the motor-stall-threshold is satisfied, the controller 150 continues to drive the motor 140 for a first predetermined duration of time. After the expiration of the first predetermined duration of time, the controller 150 communicates a third command signal to the motor 140 to reduce the duty cycle of the motor 140 to the idle state duty cycle, and the motor 140 returns to an idle state. Alternatively, based at least in part on the determination that the motor-stall-threshold is satisfied, the controller 150 can communicate a third command signal to the motor 140, which can cause the motor 140 to continue to operate for the first predetermined duration of time and then, after the expiration of the first predetermined duration of time, reduce the duty cycle of the motor 140 to the idle state duty cycle. In some cases, the third command signal can correspond to a removal of the supply of voltage to the motor 140.

Continuing to the drive the motor 140 for the first predetermined duration of time can correspond to overdriving the motor 140, which allow the finger digit 130 to exert additional gripping force on an object in its path. During this continued operation of the motor 140 after the motor-stall-threshold is satisfied, the motor 140 can consume excessive power, such as excessive current. Thus, by continuing to operate the motor 140 for only the duration of the first predetermined duration of time, the controller 150 reduces the amount of power consumed while also allowing the finger digit 130 to exert the additional gripping force on the object.

The duration of the first predetermined duration of time can vary. For example, the duration of the first predetermined duration of time can be between 10-140 ms, or some other duration. It will be understood that various other durations for the first predetermined duration of time can be utilized.

At block 520, following the expiration of the first predetermined duration of time and the reduction in duty cycle of the motor 140 to the idle state duty cycle, the controller can monitor or receive a second sensor signal from a second sensor, such as a myoelectric electrode 292 or other sensor that can be controlled by the wearer of the prosthesis 100.

At block 522, based at least in part on the second sensor signal or the monitoring of the second sensor, the controller 150 can communicate a fourth command signal to the motor 140. The fourth command signal can cause the finger digit 130 to further increase its gripping force on the object. For example, the fourth command signal can cause the motor 140 to continue to move in the direction it was moving at block 510.

In some cases, the second sensor signal corresponds to the wearer of the prosthesis 100 engaging an EMG signal for a second predetermined duration of time. In some cases, the communication of a fourth command signal to the motor 140 is further based at least in part on the user engaging the EMG signal for the second predetermined duration of time. The duration of the second predetermined duration of time can vary across embodiments. For example, the duration of the second predetermined duration of time can be between 200-800 ms, or some other duration. It will be understood that various other durations for the second predetermined duration of time can be utilized.

In some cases, the fourth command signal causing the motor 140 to operate in a cyclic or pulsing regime for a third predetermined duration of time. For example, communicating the fourth command signal to the motor 140 can include supplying voltage to the motor 140 to drive the motor 140 in a cyclic or pulsing regime. For example, in some cases, the pulsing regime can correspond to being ON for 5 to 20 ms, then off for 5 to 20 ms. As another example, the pulsing regime can correspond to being ON for 14 ms, then off for 16 ms. It will be understood that various other durations for a pulsing regime can be implemented.

The duration of the third predetermined duration of time can vary across embodiments. For example, the duration of the third predetermined duration of time can be between 0.6 to 1.4 seconds, or some other duration. It will be understood that various other durations for the third predetermined duration of time can be utilized.

It will be understood that fewer, more, or different blocks can be used as part of the routine 500B. For example, in some cases, at block 506, the controller 150 determines that the motor-stall-threshold is not satisfied. For example, the controller 150 can determine that the torque does not satisfy the torque threshold, the current drawn by the motor does not satisfy the current threshold, the voltage by the motor does not satisfy the voltage threshold, or the force on the finger digit 130 does not satisfy the force threshold. In some cases, any one or more of these conditions will cause the motor-stall-threshold to not be satisfied. In some cases, the motor-stall-threshold will not be satisfied when all of these conditions are not satisfied. If the motor-stall-threshold is not satisfied, the controller 150 can end the routine 500. Alternatively, the controller 150 can return to block 504. For example, the controller 150 can periodically or continuously receive sensor signals from the sensor(s) 160 or input device(s) 190, can compare values associated with the sensor signals to the one or more threshold to determine whether the motor-stall-threshold is satisfied.

Furthermore, the blocks of FIG. 5B can be implemented in a variety of orders, and that the prosthesis 100 can implement one or more of the blocks concurrently and/or change the order, as desired. Furthermore, fewer, more, or different blocks can be used as part of the routine 500B. For example, the routine 500B can implement some or all of various blocks of FIGS. 3, 5A, 9, or 10 in routines 300, 500A, 900, or 1000 concurrently or change the order as desired. Furthermore, the routine 500B can omit certain blocks, such as, but not limited to, blocks 518, 520, or 522. Although routine 500B is generally described with respect to moving a finger digit 130 in a flexion-closed direction, it will be understood that the routine 500B can be implemented for any movement of the finger digit 130, regardless of the direction (e.g., rotation-lateral, rotation-palmar, flexion-open, or flexion-closed) in which the first command signal causes the motor 140 to move.

Furthermore, in some cases, two motors 140 can be associated with the same finger digit 130. For example, a first motor can move a finger digit 130 in a rotation movement (e.g., any of the rotation-lateral or rotation-palmar directions), while a second motor 140 can move the finger digit 130 in a flexion movement (e.g., in any of the flexion-open or flexion-closed directions). In some cases, each of the first and second motor 140 can concurrently execute routine 500B to cause concurrent rotation and flexion movement of the finger digit 130.

Grip Force

Figure 7:
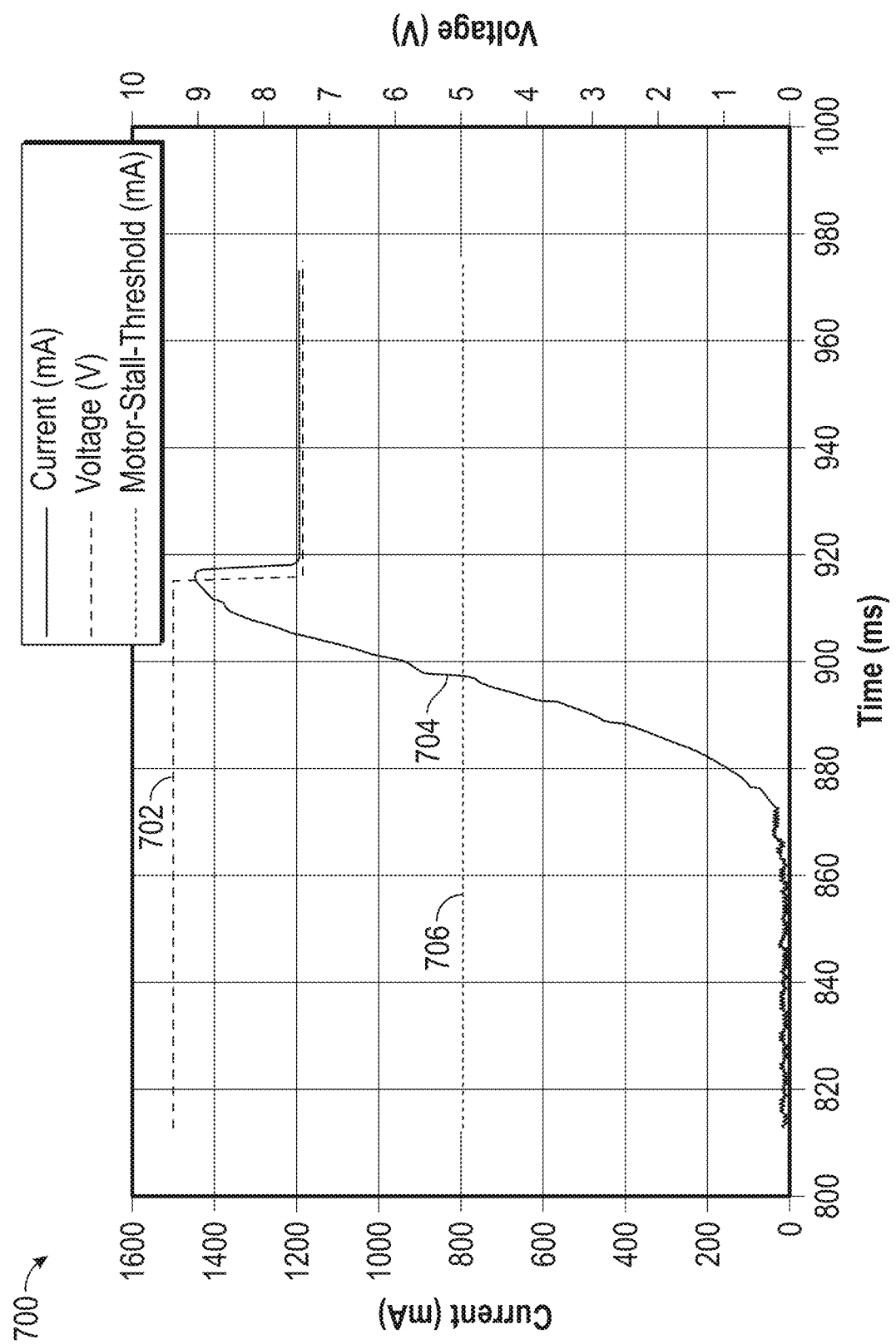
FIG. 7 is a graph illustrating example voltages and currents of a motor during an overdriving period.

As described herein, the duration of time over which the controller 150 continues to provide voltage to a motor 140 while a motor-stall-threshold is satisfied is referred to as an overdriving period. FIG. 7 is a graph 700 illustrating example voltages and currents of a motor 140 during an overdriving period. The horizontal axis on the graph 700 corresponds to time, in ms. For the voltage channel 702, the vertical axis on the graph 700 corresponds to a voltage (V), in volts, supplied to the motor. For the current channel 704 and current threshold channel 706, the vertical axis on the graph 700 corresponds to a current, in mA, drawn by the motor 140. In some cases, the graph 700 corresponds to the motor 140 moving a finger digit 130 in a flexion-closed direction. In some cases, the graph 700 corresponds to the motor 140 moving a finger digit 130 in any of a rotation-lateral, rotation-palmar, or flexion-open direction.

In the illustrated example of FIG. 7, the motor-stall-threshold corresponds to the current threshold channel 706, which is set to 800 mA. Accordingly, the motor-stall-threshold is satisfied when the current is greater than the current threshold 706. At approximately time=898 ms, the motor-stall-threshold is satisfied. In this example, the controller 150 continues to drive the motor 140 for a predetermined duration of time, which in this example is 80 ms. In some cases, this overdriving period of the motor 140 is used to allow the finger digit 130 to exert additional force on gripped objects.

Extra Grip Force

As described herein, such as with respect to blocks 512 and 514 of FIG. 65, following an overdriving of the motor 140, the controller 150 can cease the supply of voltage to the motor 140, at least for a predetermined duration. Furthermore, the controller 150 can monitor an input device(s) 190 and/or receive a signal from input device(s) 190. In some cases, based at least in part on the monitoring and/or the input signal, the controller 150 can cause the motor 140 to move to cause the finger digit 130 to exert additional force. For example, the input device(s) 190 can be a myoelectric electrode, and if the user continues to engage an EMG signal for a predetermined duration of time, the controller 150 can pulse the motor 140 to allow the finger digit 130 to exert additional force.

Figure 8:
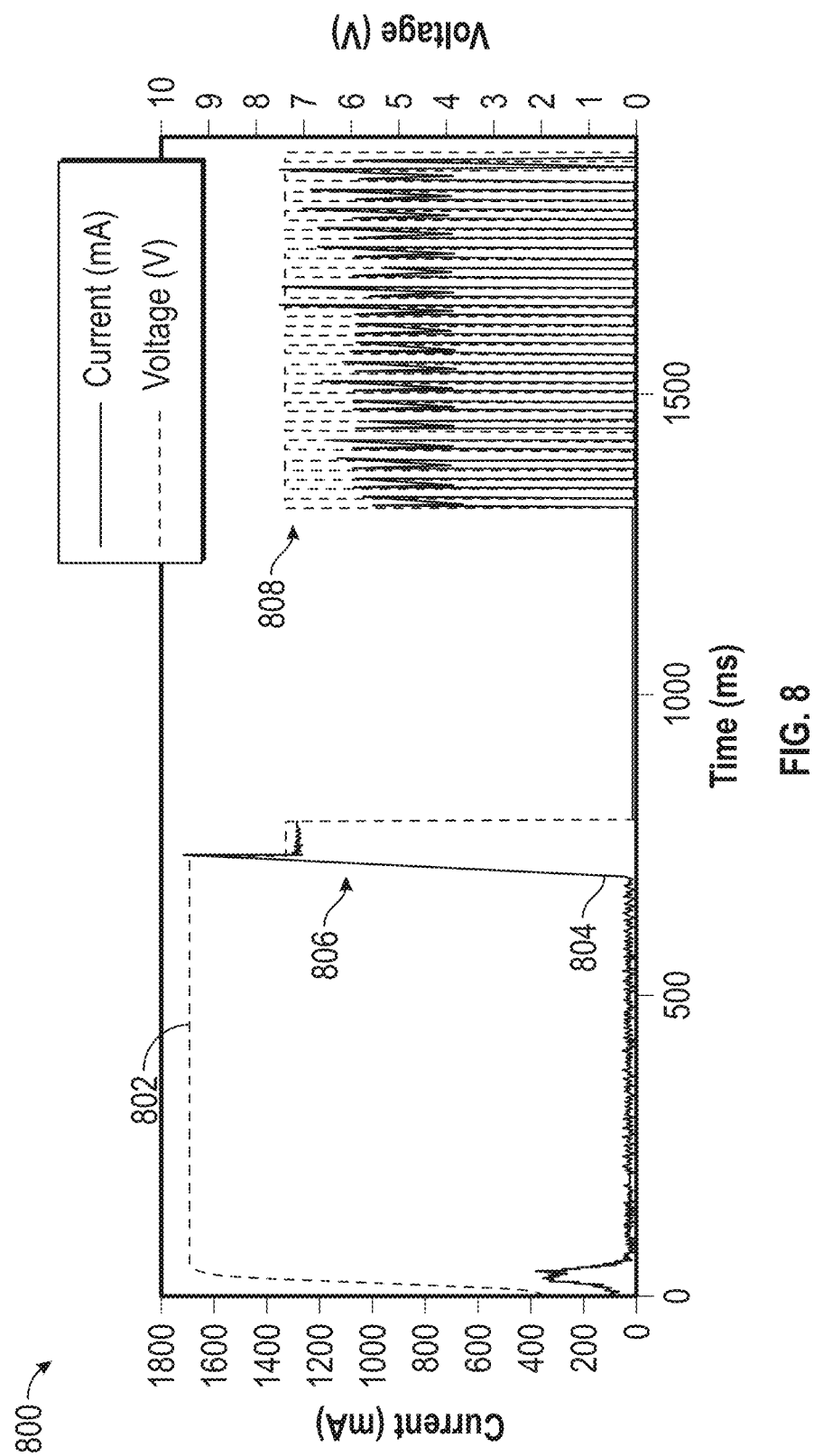
FIG. 8 is a graph illustrating an example drive profile for a motor that includes an acceleration profile, a overdriving period, and an exertion of extra force.

FIG. 8 is a graph 800 illustrating an example drive profile for a motor 140 that includes an acceleration profile, an overdriving period, and an exertion of extra force. The horizontal axis on the graph 800 corresponds to time, in ms. For the voltage channel 802, the vertical axis on the graph 800 corresponds to a voltage (V), in volts, supplied to the motor 140. For the current channel 804, the vertical axis on the graph 600 corresponds to a current, in mA, drawn by the motor 140. In some cases, the graph 700 corresponds to the motor 140 moving a finger digit 130 in a flexion-closed direction. In some cases, the graph 800 corresponds to the motor 140 moving a finger digit 130 in any of a rotation-lateral, rotation-palmar, or flexion-open direction. In the illustrated example of graph 800, prior to time=0, the motor 140 resides in an idle state, having an idle state duty cycle.

At the beginning of the drive profile, which corresponds to time=0, rather than initializing the motor 140 to start at 100% duty cycle, the motor 140 is initialized to a 20% duty cycle. This is shown by the voltage channel 802 having a value of 1.88 V at time=0 (which is 20% of the 9.4 V value at 100% duty cycle). Over the first 50 ms, the finger digit 130 is accelerated by systematically increasing the voltage supplied to the motor 140 until the motor 140 reaches a 100% duty cycle.

At a time corresponding to 806, the motor-stall-threshold is satisfied. In this example, the controller 150 continues to drive the motor 140 for a first predetermined duration of time, referred to as the overdriving period, which allows the finger digit 130 to exert additional force to further grip objects.

Following the overdriving of the motor 140, the controller 150 ceases the supply of voltage to the motor 140 and monitors an input device(s) 190, such as a myoelectric electrode. At 808, the controller 150 determines, based at least in part on an input signal of the input device(s) 190, to provide a series of pulses to the motor 140 to allow the finger digit 130 to exert additional force. After a predetermined duration of time of providing the pulses, the controller 150 ceases the supply of voltage to the motor 140.

Deceleration Profile

In some cases, a finger digit can be screwed into or otherwise attached into a knuckle block in a manner such that a range of motion of the finger digit (for example, along a flexion axis or rotation axis) is restricted between a fully-open and a fully-closed position. For instance, at both end positions, the mechanics of the finger digit and the mechanics of the knuckle block can meet each other such that the finger digit reaches (and it stopped by) a mechanical end stop at each of the fully-open and fully-closed positions.

In many prior prosthetic hands, because a position of the finger digit is not tracked, a controller can become unaware of the exact positioning of a finger digit as the finger digit is moved by the motor. For example, the motor can move the finger digit until the finger digit is stopped by a mechanical end stop (e.g., corresponding to a fully-open position), at which time the controller can determine the position of the finger digit based at least in part on a known location of the mechanical end stop. Furthermore, a starting position of the finger digit may be known or determined, for example, based at least in part on the finger digit's proximity to another mechanical end stop (e.g., corresponding to a fully-closed position). However, in general, the controller may be unaware of the exact positioning of the finger digit as it moved between mechanical end stops. At best, the position of the finger digit is estimated, for example, based at least in part on a duty cycle of the motor or a time over which the finger digit is moved. However, these estimations can be misleading and can cause the finger digit to be placed in an unintended position. For example, engineering tolerances in the manufacturing can result in varying levels of internal resistance of the prosthetic hand, such as within the motor or the finger digit. Thus, accelerations or speeds of different finger digits can vary and estimations can be difficult or inaccurate. As another example, mechanical components of the prosthetic hand can wear down over time, which can cause a change in the internal resistive forces of the prosthetic hand, thereby causing changes in acceleration or speed of the finger digit and making estimations difficult or inaccurate. As another example, dirt, grime, etc., can become lodged within the mechanics of the finger digit, which can reduce the acceleration or speed of the finger digit, thereby making estimations difficult or inaccurate.

Furthermore, the practice of continuing to drive the motor until the finger digit is stopped by a mechanical end stop reduces the prosthesis' energy efficiency. This is because the motor for the finger digit will continue to drive until a motor-stall-threshold is satisfied, which generally necessitates a rise in current drawn by the motor.

Systems, routines and methods disclosed herein can implement a deceleration profile, which can cause the finger digit 130 to decelerate as it approaches a desired position or a mechanical end-stop. Among other advantages, the implementation of a deceleration profile can reduce an amount of power consumed by a motor 140 as the motor 140 transitions from a non-idle state, for example where the motor 140 has some value of duty cycle above 0%, to an idle state, for example where the motor 140 has a duty cycle of 0%.

Systems, routines and methods disclosed herein can identify a position, such as a real-time position, of the finger digit 130. Among other advantages, the identification of the position of the finger digit 130 can allow for more precise movements of the finger digit 130, as well as the implementation of a deceleration profile, as described herein. For example, a controller 150 can determine to move the finger digit 130 from a first position to a second position, and can monitor a position of the finger digit 130 as it moves from the first position to the second position. Based at least in part on a determination that the finger digit 130 is approaching the second position (or the finger digit 130 has reached a third position between the first and second positions), the controller 150 can implement the deceleration profile, which can cause the systematic deceleration of the finger digit 130 until the finger digit 130 reaches the second position, at which time the duty cycle of the motor can be reduced to an idle state duty cycle. In some cases, the controller 150 can implement a deceleration profile on multiple motors 140 concurrently or sequentially.

Figure 9:
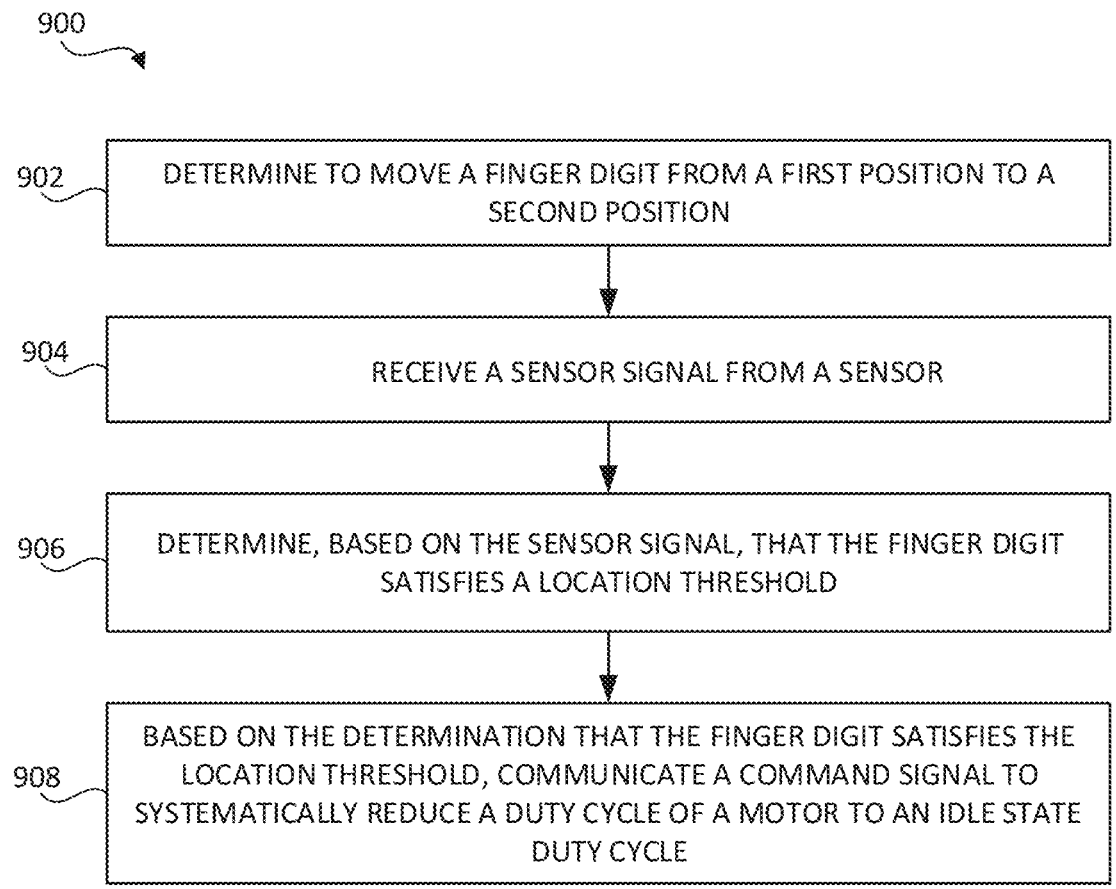
FIG. 9 is a flow diagram illustrative of a routine for an example deceleration profile implemented by a prosthesis on a motor that is configured to move a finger digit of the prosthesis.

FIG. 9 is a flow diagram illustrative of a routine 900 for an example deceleration profile implemented by a prosthesis 100 on a motor 140 that is configured to move a finger digit of the prosthesis 100. The elements outlined for routine 900 can be implemented by one or more computing devices that are associated with the prosthesis 100, such as the controller 150. Accordingly, routine 900 has been logically associated as being generally performed by the controller 150. However, the following illustrative example should not be construed as limiting.

At block 902, similar to block 302 of FIG. 3, the controller 150 determines to move the finger digit 130 from a first position to a second position.

At block 904, the controller 150 receives a sensor signal from a sensor(s) 160. The sensor(s) 160 can capture information relating to, among other things, position or movement of the motor 106 or the finger digit 130, and the sensor signal can correspond to some or all of this information. In some cases, the sensor 130 can correspond to a position sensor, such as a Hall Effect sensor or a rotary encoder, as described herein.

At block 906, the controller 150 determines, based at least in part on the sensor signal, that the finger digit 130 satisfies a location threshold. For example, as the motor 140 moves the finger digit 130 from the first position (e.g., the starting position of the finger digit 130) to the second position (e.g., the desired ending position of the finger digit 130), the controller 150 can utilize the sensor signal received at block 906 to determine the real-time position of the finger digit 130, such as an absolute position, a relative position, or an angular position of the finger digit.

In some cases, the location threshold can correspond to a third position of the finger digit 130, which can be a position located between the first position and the second position. For example, based at least in part on a determination that the finger digit 130 has reached or is at the third position, the controller 150 can determine that the location threshold is satisfied.

In some cases, the location threshold can correspond to a position with respect to the second position. For example, the location threshold can be a certain distance or a particular angular distance away from the second position. As such, based at least in part on a determination that the finger digit 130 is within the certain distance or the particular angular distance from the second position, the controller 150 can determine that the location threshold is satisfied.

At block 908, the controller 150 communicates a command signal to systematically reduce a duty cycle of the motor to an idle state duty cycle. The communication of the command signal can be based at least in part on the determination that the finger digit 130 satisfies the location threshold.

The systematic decrease in the duty cycle can include a gradual or controlled decrease in the duty cycle to the idle state duty cycle. In some cases, the systematic decrease can be a uniform decrease to the idle state duty cycle. In certain cases, the systematic decrease can be non-uniform decrease to the idle state duty cycle. In some cases, the systematic decrease includes a stepwise decrease. For example, the duty cycle of the motor can be decreased in a stepwise pattern from its operating duty cycle to the idle state duty cycle, for example, including 5, 8, 10, 12, 15, or 20 "steps" or discrete points in the stepwise pattern. In some cases, the systematic decrease, such as the stepwise pattern, corresponds to a reverse S-shaped exponential curve or a reverse J-shaped exponential curve.

The systematic decrease in the duty cycle of the motor 140 to the idle state duty cycle can occur over a predetermined duration of time. The length of the predetermined duration of time can vary across embodiments. For example, the length of the first predetermined duration of time can be between 20-140 ms, or some other duration. It will be understood that various other durations can be utilized.

It will be understood that the various blocks of FIG. 9 can be implemented in a variety of orders, and that the prosthesis 100 can implement one or more of the blocks concurrently and/or change the order, as desired. Furthermore, it will be understood that fewer, more, or different blocks can be used as part of the routine 900. For example, the routine 900 can include blocks for implementing an acceleration profile, as described herein. For example, the controller 150 can communicate another command signal. Similar to as described in block 304 of FIG. 3, prior to the communication of another command signal, the motor 140 can be in an idle state. Furthermore, similar to as described in block 304 of FIG. 3, the command signal can cause a duty cycle of the motor 140 to increase from the idle state duty cycle to some value of duty cycle above 0%. Similar to blocks 304 and 306 of FIG. 3, the another command signal can cause a duty cycle of the motor 140 to increase from the idle state duty cycle to satisfy a first duty cycle level that allows the motor 140 to overcome the stiction of the motor 140, and the another command signal can further cause a systematic increase in the duty cycle of the motor 140 from the first duty cycle level to another duty cycle level.

As another example, the controller 150 can communicate another command signal to vary the duty cycle of the motor in proportion to one or more sensor signals received from a myoelectric sensor. In some cases, based on a determination that a motor-stall-threshold is satisfied, the controller 150 can communicate a command signal to reduce the duty cycle until the motor-stall-threshold is no longer satisfied. For example, the desired force of the finger digit 130 may be determined or set based at least in part on a strength of an input signal received from an input device(s) 190. In some cases, the controller 150 can communicate a command signal to control the duty cycle of the motor 140 to achieve this desired force. However, based at least in part on a satisfaction of a motor-stall-threshold, the controller 150 can communicate a command signal to reduce the duty cycle of the motor 140, thereby reducing the current consumption such that the motor-stall-threshold is no longer satisfied. The controller 150 can continue to drive the motor 140 as this reduced duty cycle for a duration of time.

Furthermore, the routine 900 can implement some or all of various blocks of FIGS. 3, 5A, 5B, or 10 in routines 300, 500A, 500B, or 1000 concurrently or change the order as desired. Furthermore, the routine 900 can omit certain blocks, such as, but not limited to, blocks 902, 904, 906, or 908. For example, in some cases, the controller 150 does not determine to move the finger digit 130.

Furthermore, in some cases, two motors 140 can be associated with the same finger digit 130. For example, a first motor can move a finger digit 130 in a rotation movement (e.g., any of the rotation-lateral or rotation-palmar directions), while a second motor 140 can move the finger digit 130 in a flexion movement (e.g., in any of the flexion-open or flexion-closed directions). In some cases, each of the first and second motor 140 can concurrently execute routine 900 to cause concurrent rotation and flexion movement of the finger digit 130.

Acceleration and Deceleration Profiles

Figure 10:
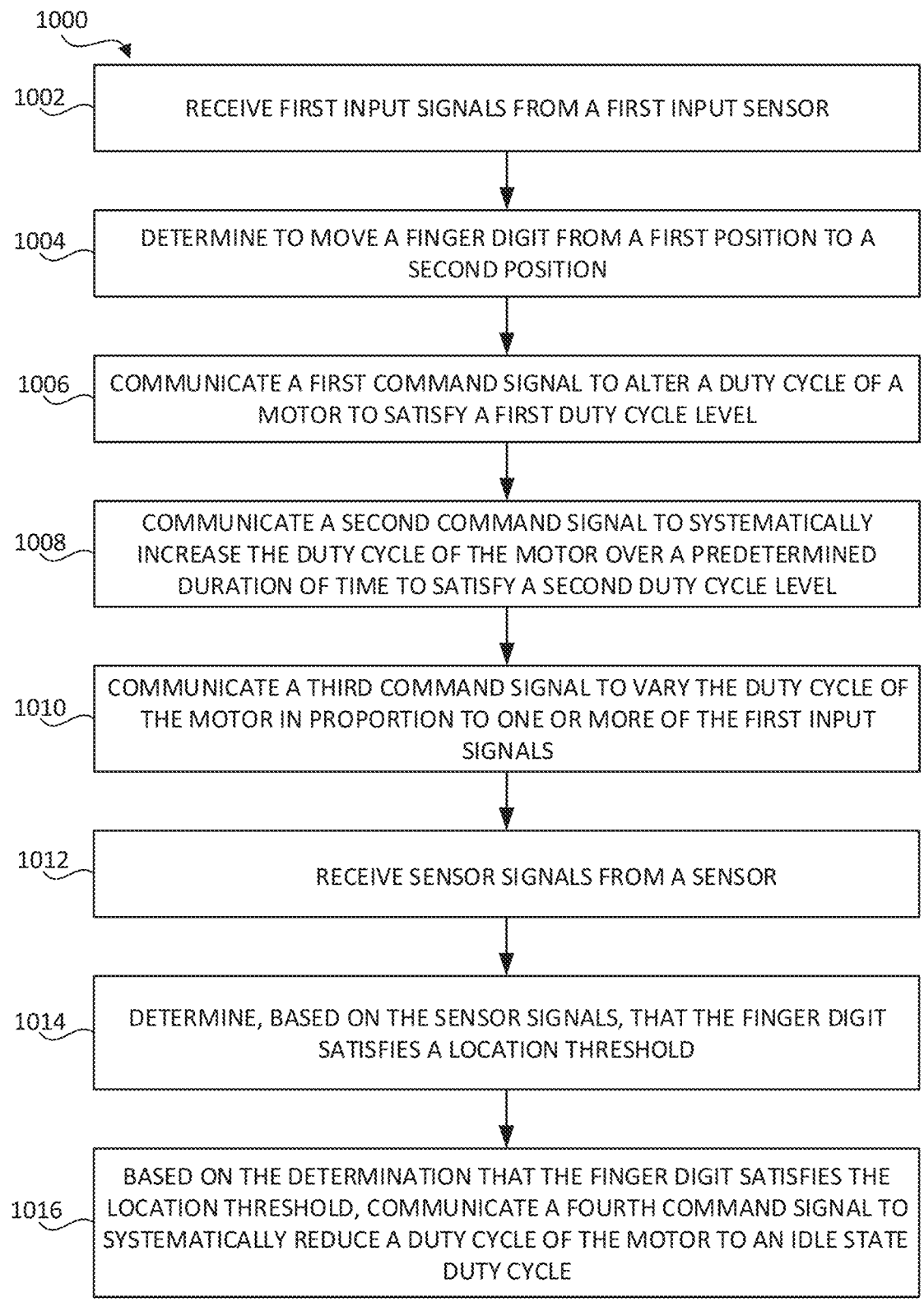
FIG. 10 is a flow diagram illustrative of a routine for an example acceleration and deceleration profile implemented by a prosthesis on a motor that is configured to move a finger digit of the prosthesis.

FIG. 10 is a flow diagram illustrative of a routine 1000 for an example acceleration and deceleration profile implemented by a prosthesis 100 on a motor 140 that is configured to move a finger digit of the prosthesis 100. The elements outlined for routine 1000 can be implemented by one or more computing devices that are associated with the prosthesis 100, such as the controller 150. Accordingly, routine 1000 has been logically associated as being generally performed by the controller 150. However, the following illustrative example should not be construed as limiting.

At block 1002, the controller 150 receives first signals from an input device(s) 190. In some cases, the first signals are received from a myoelectric electrode. For example, a myoelectric electrode can detect electric activity from a muscle of a wearer of the prosthesis 100, and the myoelectric electrode can relay that information to the controller 150.

At block 1004, similar to blocks 302 of FIG. 3 or 902 of FIG. 9, the controller 150 determines to move a finger digit 130 from a first position to a second position.

At block 1006, similar to blocks 304 of FIG. 3, the controller 150 communicates a first command signal to alter a duty cycle of a motor to satisfy a first duty cycle level.

At block 1008, similar to blocks 306 of FIG. 3, the controller 150 communicates a second command signal to systematically increase the duty cycle of the motor over a first predetermined duration of time to satisfy a second duty cycle level.

At block 1010, the controller 150 communicates a third command signal to vary the duty cycle of the motor in proportion to one or more of the first sensor signals received from the myoelectric sensor.

At block 1012, similar to block 904 of FIG. 9, the controller 150 receives second sensor signals from a second sensor(s) 160. The second sensor(s) 160 can capture information relating to, among other things, position or movement of the motor 106 or the finger digit 130, and the second sensor signals can correspond to some or all of this information. In some cases, the second sensor 130 can correspond to a position sensor, such as a Hall Effect sensor or a rotary encoder, as described herein.

At block 1014, similar to block 906 of FIG. 9, the controller 150 determines, based at least in part on the second sensor signals, that the finger digit 130 satisfies a location threshold.

At block 1016, similar to block 908 of FIG. 9, the controller 150 communicates a fourth command signal to systematically reduce a duty cycle of the motor to an idle state duty cycle.

It will be understood that the various blocks of FIG. 10 can be implemented in a variety of orders, and that the prosthesis 100 can implement one or more of the blocks concurrently and/or change the order, as desired. For example, the controller 150 can receive the first or second sensor signals at any point during routine 1000. Furthermore, it will be understood that fewer, more, or different blocks can be used as part of the routine 1000. The routine 1000 can implement some or all of various blocks of FIGS. 3, 5A, 5B, or 9 in routines 300, 500A, 500B, or 900 concurrently or change the order as desired. Furthermore, the routine 1000 can omit certain blocks, such as, but not limited to, blocks 1002, 1004, 1010, or 1012.

Furthermore, in some cases, two motors 140 can be associated with the same finger digit 130. For example, a first motor can move a finger digit 130 in a rotation movement (e.g., any of the rotation-lateral or rotation-palmar directions), while a second motor 140 can move the finger digit 130 in a flexion movement (e.g., in any of the flexion-open or flexion-closed directions). In some cases, each of the first and second motor 140 can concurrently execute routine 1000 to cause concurrent rotation and flexion movement of the finger digit 130.

Example Drive Profiles

Figure 11:
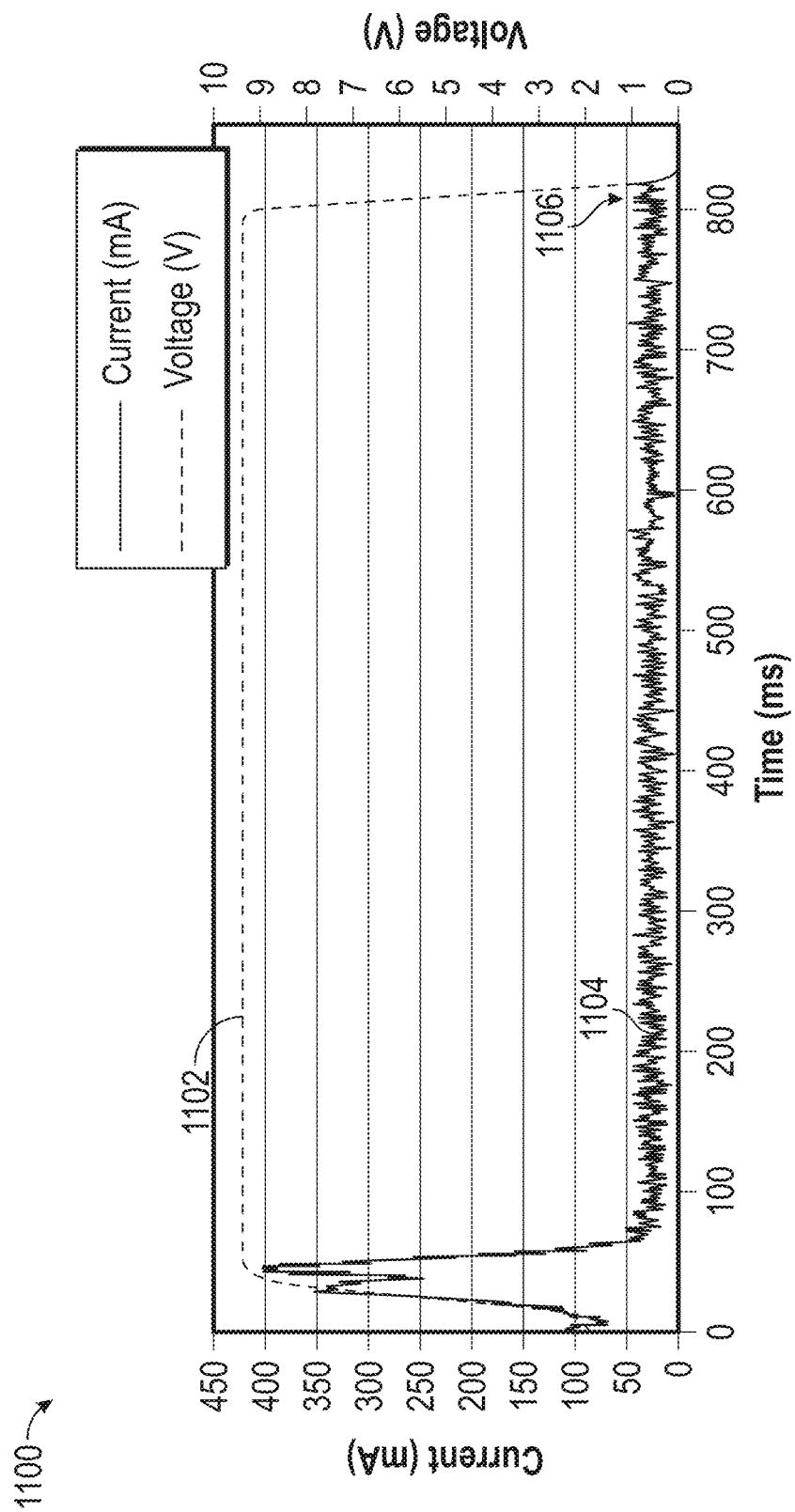
FIG. 11 is a graph illustrating an example drive profile for a motor that includes an acceleration profile and a deceleration profile.

FIG. 11 is a graph 1100 illustrating an example drive profile for a motor 140 that includes an acceleration profile and a deceleration profile. The horizontal axis on the graph 1100 corresponds to time, in ms. For the voltage channel 1102, the vertical axis on the graph 1100 corresponds to a voltage (V), in volts, supplied to the motor 140. For the current channel 1104, the vertical axis on the graph 1100 corresponds to a current, in mA, drawn by the motor 140. In some cases, the graph 1100 corresponds to the motor 140 moving a finger digit 130 in a flexion-closed direction. In some cases, the graph 1100 corresponds to the motor 140 moving a finger digit 130 in any of a rotation-lateral, rotation-palmar, or flexion-open direction. In the illustrated example of graph 1100, prior to time=0, the motor 140 resides in an idle state, having an idle state duty cycle.

At the beginning of the drive profile, which corresponds to time=0, rather than initializing the motor 140 to start at 100% duty cycle, the motor 140 is initialized to a 20% duty cycle. This is shown by the voltage channel 1102 having a value of approximately 1.88 V at time=0 (which is 20% of the 9.4 V value at 100% duty cycle). Over the first 50 ms, the finger digit 130 is accelerated by systematically increasing the voltage supplied to the motor 140 until the motor 140 reaches a 100% duty cycle. In the illustrated example, after the finger digit is accelerated, the voltage remains constant for a duration of time until the duty cycle of the motor 140 is systematically decreased by the controller 150 to 0%. As described herein, in some cases, the controller 150 can determine to systematically decrease the duty cycle of the motor 140 based on a determination that a position of the finger digit 130 satisfies a position threshold. For example, in the illustrated example, using data from a position sensor, the controller 150 determined that the finger digit 130 satisfied the position threshold and, based on that determination, initiated a deceleration profile, as described herein. In some cases, at the end of the deceleration profile, the finger digit 130 is located at a mechanical end-stop. As illustrated by a comparison to FIG. 8, the drive profile of FIG. 11 advantageously increases an energy efficiency of the prosthesis 100 by reducing an amount of energy consumed by the motor 140 as the motor 140 nears the mechanical end-stop.

Figure 12:
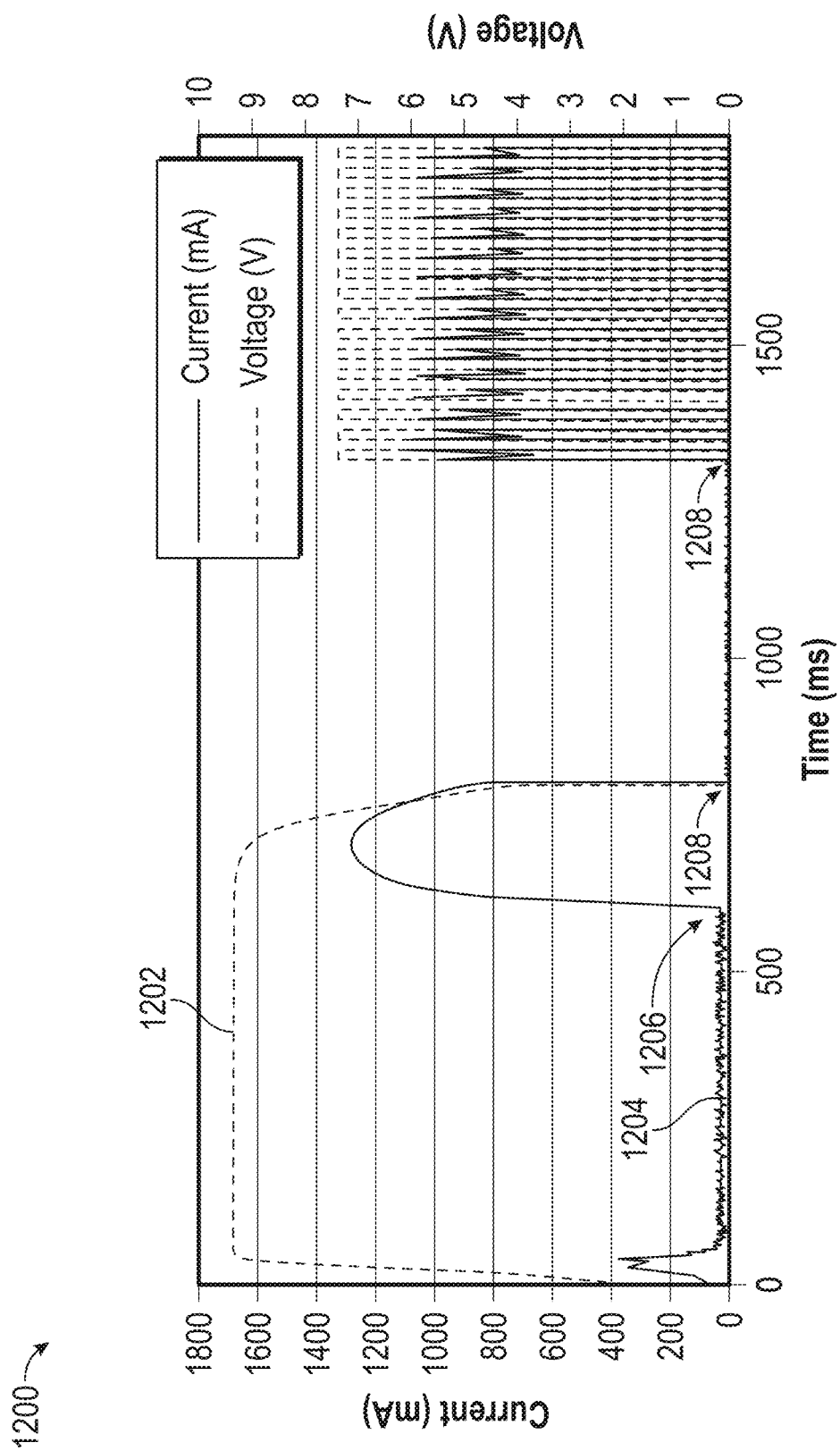
FIG. 12 is a graph illustrating an example drive profile for a motor that includes an acceleration profile, a deceleration profile, an overdriving period, and the exertion of extra force.

FIG. 12 is a graph 1200 illustrating an example drive profile for a motor 140. The horizontal axis on the graph 1200 corresponds to time, in ms. For the voltage channel 1202, the vertical axis on the graph 1200 corresponds to a voltage (V), in volts, supplied to the motor 140. For the current channel 1204, the vertical axis on the graph 1200 corresponds to a current, in mA, drawn by the motor 140. In some cases, the graph 1200 corresponds to the motor 140 moving a finger digit 130 in a flexion-closed direction. In some cases, the graph 1200 corresponds to the motor 140 moving a finger digit 130 in any of a rotation-lateral, rotation-palmar, or flexion-open direction. In the illustrated example of graph 1200, prior to time=0, the motor 140 resides in an idle state, having an idle state duty cycle.

At the beginning of the drive profile, which corresponds to time=0, rather than initializing the motor 140 to start at 100% duty cycle, the motor 140 is initialized to start at a first duty cycle level. Over a first predetermined duration of time, the finger digit 130 is accelerated by systematically increasing the duty cycle of the motor from the first duty cycle level to a second duty cycle level.

At the time corresponding to 1206, the current starts to increase, for example, responsive to the finger digit 130 contacting an object. As the current continues to increase, the controller 150 can determine that a motor-stall-threshold is satisfied. However, in contrast to graph 600 of FIG. 6, rather than causing the duty cycle to immediately reduce to a 0% duty cycle, the controller 150 communicates a command signal to reduce the duty cycle until the motor-stall-threshold is no longer satisfied. This allows the motor 140 to continue to run for a duration of time, without consuming as much energy as if the motor 140 was operated at 100% duty cycle. Nonetheless, by continuing the provide the motor 140 a duty cycle greater than a 0% duty cycle, the motor 140 continues to the move the finger digit 130, which further increases a force grip of the finger digit 130 on the object.

At the time corresponding to 1208, the controller 150 causes the end of the supply of voltage to the motor 140 and monitors an input device(s) 190, such as a myoelectric electrode. At 1208, the controller 150 determines, based at least in part on an input signal from the input device(s) 190, to provide a series of pulses to the motor 140 to allow the finger digit 130 to exert additional force. After a predetermined duration of time of providing the pulses, the controller 150 ceases the supply of voltage to the motor 140.

Example Embodiments

Various example embodiments of methods, systems or non-transitory computer-readable medium relating to reducing electromagnetic interference or conserving power in a prosthetic device can be found in the following clauses:

Clause 1. A prosthetic device, comprising:
a finger digit;
a motor configured to move the finger digit based at least in part on one or more command signals received from a controller, wherein the controller is configured to:
determine, based at least in part on a command signal, to move the finger digit,
communicate a first command signal to alter a duty cycle of the motor to satisfy a first duty cycle level to overcome stiction associated with one or more components of the motor, and based at least in part on a determination that the duty cycle of the motor satisfies the first duty cycle level, communicate a second command signal to systematically increase the duty cycle of the motor over a predetermined duration of time to satisfy a second duty cycle level.

Clause 2. The prosthetic device of Clause 1, wherein the systematic increase comprises a linear increase over the predetermined duration of time from the first duty cycle level to the second duty cycle level.

Clause 3. The prosthetic device of any of the previous clauses, wherein the systematic increase comprises a uniform increase over the predetermined duration of time from the first duty cycle level to the second duty cycle level.

Clause 4. The prosthetic device of any of the previous clauses, wherein the systematic increase comprises a non-uniform increase over the predetermined duration of time from the first duty cycle level to the second duty cycle level.

Clause 5. The prosthetic device of any of the previous clauses, wherein the systematic increase comprises a stepwise increase over the predetermined duration of time from the first duty cycle level to the second duty cycle level.

Clause 6. The prosthetic device of any of the previous clauses, wherein the systematic increase corresponds to an S-shaped growth curve.

Clause 7. The prosthetic device of any of the previous clauses, wherein the systematic increase corresponds to a J-shaped growth curve.

Clause 8. The prosthetic device of any of the previous clauses, wherein the command signal corresponds to one or more of the sensor signals from a myoelectric sensor.

Clause 9. The prosthetic device of Clause 8, further comprising the myoelectric sensor, wherein the myoelectric sensor is configured to sense electric activity of a muscle of a wearer of the prosthetic device, wherein the controller is further configured to receive the one or more sensor signals from the myoelectric sensor.

Clause 10. The prosthetic device of any of the previous clauses, wherein the controller stores computer executable instructions that when executed by one or more processors cause the controller to communicate the first command signal.

Clause 11. The prosthetic device of any of the previous clauses, wherein to determine to move the finger digit, the controller is configured to move the finger digit from a first position to a second position.

Clause 12. The prosthetic device of Clause 11, wherein the first position corresponds to a fully extended position of the finger digit and the second position corresponds to a fully flexed position of the finger digit.

Clause 13. The prosthetic device of Clause 11, wherein the first position corresponds to a fully flexed position of the finger digit and the second position corresponds to a fully extended position of the finger digit.

Clause 14. The prosthetic device of any of the previous clauses, wherein the first duty cycle level corresponds to a value of duty cycle 15% and 25%.

Clause 15. The prosthetic device of any of the previous clauses, wherein the first duty cycle level corresponds to a 20% duty cycle.

Clause 16. The prosthetic device of any of the previous clauses, wherein the second duty cycle level corresponds to a value of duty cycle above 0%.

Clause 17. The prosthetic device of any of the previous clauses, wherein the second duty cycle level corresponds to a value of duty cycle above 20%.

Clause 18. The prosthetic device of any of the previous clauses, wherein the second duty cycle level corresponds to a value of duty cycle between 20% and 100%.

Clause 19. The prosthetic device of any of the previous clauses, wherein the second duty cycle level corresponds to a value of duty cycle above 100%.

Clause 20. The prosthetic device of any of the previous clauses, wherein the second duty cycle level corresponds to a 100% duty cycle.

Clause 21. The prosthetic device of any of the previous clauses, wherein the pre-determined duration of time comprises between 20 milliseconds and 150 milliseconds.

Clause 22. The prosthetic device of any of the previous clauses, wherein the pre-determined duration of time comprises 100 milliseconds.

Clause 23. The prosthetic device of any of the previous clauses, wherein the controller is further configured to:
based at least in part on a determination that the predetermined duration of time has lapsed, communicate a third command signal to vary the duty cycle of the motor in proportion to one or more sensor signals received from a myoelectric sensor.

Clause 24. The prosthetic device of any of the previous clauses, wherein the controller is further configured to:
based at least in part on a determination that a motor-stall-threshold is satisfied, communicate a fourth command signal to decrease the duty cycle of the motor to an idle state duty cycle.

Clause 25. The prosthetic device of Clause 24, wherein the idle state duty cycle corresponds to a value of duty cycle below 20%.

Clause 26. The prosthetic device of any of Clauses 24 or 25, wherein the idle state duty cycle corresponds to a value of duty cycle below 10%.

Clause 27. The prosthetic device of any of Clauses 24 to 26, wherein the idle state duty cycle corresponds to a value of duty cycle below 5%.

Clause 28. The prosthetic device of any of Clauses 24 to 27, wherein the idle state duty cycle corresponds to a 0% duty cycle.

Clause 29. The prosthetic device of any of Clauses 24-28, wherein the controller is further configured to:

determine that the motor-stall-threshold is satisfied based at least in part on a torque of the motor, a current drawn by the motor, a voltage of the motor, or a force acting on the finger digit.

Clause 30. The prosthetic device of any of Clauses 24-29, wherein the controller is further configured to:

receive a sensor signal indicative of a current drawn by the motor;

compare the current drawn by the motor to a current threshold; and determine that the motor-stall-threshold is satisfied based at least in part on a determination that the current drawn by the motor satisfies the current threshold.

Clause 31. The prosthetic device of Clause 30, wherein the current threshold is between 600 mA and 1 A.

Clause 32. The prosthetic device of any of Clauses 30 or 31, wherein the current threshold is between 650 mA and 750 mA.

Clause 33. The prosthetic device of any of Clauses 30 to 32, wherein the current threshold is 700 mA.

Clause 34. The prosthetic device of any of Clauses 30 or 31, wherein the current threshold is between 750 mA and 850 mA.

Clause 35. The prosthetic device of any of Clauses 30, 31, or 34, wherein the current threshold is 800 mA.

Clause 36. The prosthetic device of any of Clauses 24-29, wherein the controller is further configured to:

receive a sensor signal indicative of a voltage drawn by the motor;

compare the voltage drawn by the motor to a voltage threshold; and determine that the motor-stall-threshold is satisfied based at least in part on a determination that the voltage drawn by the motor satisfies the voltage threshold.

Clause 37. The prosthetic device of any of Clauses 24-29, wherein the controller is further configured to:

receive a sensor signal indicative of a torque of the motor;

compare the torque of the motor to a torque threshold; and determine that the motor-stall-threshold is satisfied based at least in part on a determination that the torque of the motor satisfies the torque threshold.

Clause 38. The prosthetic device of any of Clauses 24-29, wherein the controller is further configured to:

receive a sensor signal indicative of a force at the finger digit;

compare the force at the finger digit to a force threshold; and determine that the motor-stall-threshold is satisfied based at least in part on a determination that the force at the finger digit satisfies the force threshold.

Clause 39. The prosthetic device of Clause 38, wherein the sensor signal is received from one or more capacitive or inductive force sensors.

Clause 40. The prosthetic device of Clause 39, wherein the one or more capacitive or inductive force sensors are located in a finger pad of the finger digit.

Clause 41. The prosthetic device of any of Clauses 24-40, wherein to communicate the third command signal to decrease the duty cycle of the motor to the idle state duty cycle, the controller is further configured to communicate the third command signal to decrease the duty cycle of the motor to the idle state duty cycle based at least in part on a determination that the predetermined duration of time has lapsed.

Clause 42. The prosthetic device of any of Clauses 24-41, wherein the predetermined duration of time is a first predetermined duration of time, wherein to communicate the fourth command signal to decrease the duty cycle of the motor to the idle state duty cycle, the controller is further configured to communicate the fourth command signal to decrease the duty cycle of the motor to the idle state duty cycle based at least in part on a determination that a second predetermined duration of time has elapsed since the motor-stall-threshold was satisfied.

Clause 43. The prosthetic device of Clause 42, wherein the second pre-determined duration of time comprises between 20 ms and 150 ms.

Clause 44. The prosthetic device of Clause 42, wherein the second pre-determined duration of time comprises 80 ms.

Clause 45. The prosthetic device of any of the previous clauses, wherein the controller is further configured to communicate a fifth command signal to provide a series of pulses to the motor.

Clause 46. The prosthetic device of Clauses 45, wherein to communicate the fifth command signal, the controller is further configured to communicate the fifth command signal based at least in part on a determination that the first predetermined duration of time has lapsed.

Clause 47. The prosthetic device of any of Clauses 45 or 46, wherein to communicate the fifth command signal, the controller is further configured to communicate the fifth command signal based at least in part on a determination that a motor-stall-threshold is satisfied.

Clause 48. The prosthetic device of any of Clauses 45 to 47, wherein to communicate the fifth command signal, the controller is further configured to communicate the fifth command signal based at least in part on a determination that a sensor signal from a myoelectric sensor satisfies a sensor grip threshold.

Clause 49. The prosthetic device of Clauses 48, wherein the sensor grip threshold corresponds to a user engaging a muscle of the wearer of the prosthetic device for a third predetermined duration of time.

Clause 50. The prosthetic device of Clauses 49, wherein the third predetermined duration of time comprises 500 milliseconds.

Clause 51. The prosthetic device of Clauses 45, wherein the series of pulses are communicated to the motor over a one second time interval.

Clause 52. The prosthetic device of any of the previous clauses, wherein the controller is further configured to:

based at least in part on a determination that that the finger digit satisfies a location threshold with respect to the second position, communicate one or more command signals to systematically decrease a duty cycle of the motor until the finger digit reaches the second position.

Clause 53. The prosthetic device of Clause 52, wherein the controller is further configured to:

receive one or more sensors signals from a position sensor, and determine a real-time position of the finger digit based at least in part on the one or more sensor signals, wherein the determination that the finger digit satisfies the location threshold with respect to the second position is based at least in part on the real-time position of the finger digit.

Clause 54. The prosthetic device of any of Clauses 52 or 53, further comprising a position sensor usable to identify a position of the finger digit.

Clause 55. The prosthetic device of Clause 54, wherein the position sensor comprises a Hall Effect sensor.

Clause 56. The prosthetic device of any of Clauses 52 to 55, wherein the systematic decrease occurs over a predetermined duration of time.

Clause 57. The prosthetic device of any of Clauses 52 to 56, wherein the systematic decrease reduces the duty cycle to an idle state duty cycle when the finger digit reaches the second position.

Clause 58. The prosthetic device of any of Clauses 52 to 57, wherein the systematic decrease comprises a linear decrease.

Clause 59. The prosthetic device of any of Clauses 52 to 58, wherein the systematic decrease comprises a uniform decrease.

Clause 60. The prosthetic device of any of Clauses 52 to 59, wherein the systematic decrease comprises a non-uniform decrease.

Clause 61. The prosthetic device of any of Clauses 52 to 60, wherein the systematic decrease comprises a stepwise decrease.

Clause 62. The prosthetic device of any of Clauses 52 to 61, wherein the systematic decrease corresponds to a reverse S-shaped decay curve.

Clause 63. The prosthetic device of any of Clauses 52 to 62, wherein the systematic increase corresponds to a reverse J-shaped decay curve.

Example Embodiments

Various example embodiments of methods, systems or non-transitory computer-readable medium relating to reducing electromagnetic interference or conserving power in a prosthetic device can be found in the following clauses:

Clause 1. A method of reducing electromagnetic interference or conserving power in a prosthetic device comprising a finger digit and a motor configured to move the finger digit, comprising:
determining, based at least in part on a command signal, to move the finger digit;
communicating a first command signal to alter a duty cycle of the motor to satisfy a first duty cycle level to overcome stiction associated with one or more components of the motor, and based at least in part on a determination that the duty cycle of the motor satisfies the first duty cycle level, communicating a second command signal to systematically increase the duty cycle of the motor over a predetermined duration of time to satisfy a second duty cycle level.

Clause 2. The method of Clause 1, wherein the systematic increase comprises a linear increase over the predetermined duration of time from the first duty cycle level to the second duty cycle level.

Clause 3. The method of any of the previous clauses, wherein the systematic increase comprises a uniform increase over the predetermined duration of time from the first duty cycle level to the second duty cycle level.

Clause 4. The method of any of the previous clauses, wherein the systematic increase comprises a non-uniform increase over the predetermined duration of time from the first duty cycle level to the second duty cycle level.

Clause 5. The method of any of the previous clauses, wherein the systematic increase comprises a stepwise increase over the predetermined duration of time from the first duty cycle level to the second duty cycle level.

Clause 6. The method of any of the previous clauses, wherein the systematic increase corresponds to an S-shaped growth curve.

Clause 7. The method of any of the previous clauses, wherein the systematic increase corresponds to a J-shaped growth curve.

Clause 8. The method of any of the previous clauses, wherein the command signal corresponds to one or more of the sensor signals from a myoelectric sensor.

Clause 9. The method of Clause 8, further comprising receiving one or more sensor signals from a myoelectric sensor, wherein the myoelectric sensor is configured to sense electric activity of a muscle of a wearer of a prosthetic device.

Clause 10. The method of any of the previous clauses, wherein determining to move the finger digit comprising determining to move the finger digit from a first position to a second position.

Clause 11. The method of Clause 10, wherein the first position corresponds to a fully extended position of the finger digit and the second position corresponds to a fully flexed position of the finger digit.

Clause 12. The method of Clause 10, wherein the first position corresponds to a fully flexed position of the finger digit and the second position corresponds to a fully extended position of the finger digit.

Clause 13. The method of any of the previous clauses, wherein the first duty cycle level corresponds to a value of duty cycle 15% and 25%.

Clause 14. The method of any of the previous clauses, wherein the first duty cycle level corresponds to a 20% duty cycle.

Clause 15. The method of any of the previous clauses, wherein the second duty cycle level corresponds to a value of duty cycle above 0%.

Clause 16. The method of any of the previous clauses, wherein the second duty cycle level corresponds to a value of duty cycle above 20%.

Clause 17. The method of any of the previous clauses, wherein the second duty cycle level corresponds to a value of duty cycle between 20% and 100%.

Clause 18. The method of any of the previous clauses, wherein the second duty cycle level corresponds to a value of duty cycle above 100%.

Clause 19. The method of any of the previous clauses, wherein the second duty cycle level corresponds to a 100% duty cycle.

Clause 20. The method of any of the previous clauses, wherein the pre-determined duration of time comprises between 20 milliseconds and 150 milliseconds.

Clause 21. The method of any of the previous clauses, wherein the pre-determined duration of time comprises 100 milliseconds.

Clause 22. The method of any of the previous clauses, further comprising:
based at least in part on a determination that the predetermined duration of time has lapsed, communicating a third command signal to vary the duty cycle of the motor in proportion to one or more sensor signals received from a myoelectric sensor.

Clause 23. The method of any of the previous clauses, further comprising:

based at least in part on a determination that a motor-stall-threshold is satisfied, communicating a fourth command signal to decrease the duty cycle of the motor to an idle state duty cycle.

Clause 24. The method of Clause 23, wherein the idle state duty cycle corresponds to a value of duty cycle below 20%.

Clause 25. The method of any of Clauses 23 or 24, wherein the second duty cycle level corresponds to a value of duty cycle below 10%.

Clause 26. The method of any of Clauses 23 to 25, wherein the second duty cycle level corresponds to a value of duty cycle below 5%.

Clause 27. The method of any of Clauses 23 to 26, wherein the second duty cycle level corresponds to a 0% duty cycle.

Clause 28. The method of any of Clauses 23-27, further comprising:

determining that the motor-stall-threshold is satisfied based at least in part on a torque of the motor, a current drawn by the motor, a voltage of the motor, or a force acting on the finger digit.

Clause 29. The method of any of Clauses 23-28, further comprising:

receiving a sensor signal indicative of a current drawn by the motor;

comparing the current drawn by the motor to a current threshold; and determining that the motor-stall-threshold is satisfied based at least in part on a determination that the current drawn by the motor satisfies the current threshold.

Clause 30. The method of Clause 29, wherein the current threshold is between 600 mA and 1 A.

Clause 31. The method of any of Clauses 29 or 30, wherein the current threshold is between 650 mA and 750 mA.

Clause 32. The method of any of Clauses 29 to 31, wherein the current threshold is 700 mA.

Clause 33. The method of any of Clauses 29 or 30, wherein the current threshold is between 750 mA and 850 mA.

Clause 34. The method of any of Clauses 29, 30, or 33, wherein the current threshold is 800 mA.

Clause 35. The method of any of Clauses 23-28, further comprising:

receiving a sensor signal indicative of a voltage drawn by the motor;

comparing the voltage drawn by the motor to a voltage threshold; and determining that the motor-stall-threshold is satisfied based at least in part on a determination that the voltage drawn by the motor satisfies the voltage threshold.

Clause 36. The method of any of Clauses 23-28, further comprising:

receiving a sensor signal indicative of a torque of the motor;

comparing the torque of the motor to a torque threshold; and determining that the motor-stall-threshold is satisfied based at least in part on a determination that the torque of the motor satisfies the torque threshold.

Clause 37. The method of any of Clauses 24-29, further comprising:

receiving a sensor signal indicative of a force at the finger digit;

comparing the force at the finger digit to a force threshold; and determining that the motor-stall-threshold is satisfied based at least in part on a determination that the force at the finger digit satisfies the force threshold.

Clause 38. The method of Clause 37, wherein the sensor signal is received from one or more capacitive or inductive force sensors.

Clause 39. The method of Clause 38, wherein the one or more capacitive or inductive force sensors are located in a finger pad of the finger digit.

Clause 40. The method of any of Clauses 23-39, wherein communicating the third command signal to decrease the duty cycle of the motor to the idle state duty cycle is based at least in part on a determination that the predetermined duration of time has lapsed.

Clause 41. The method of any of Clauses 23-40, wherein the predetermined duration of time is a first predetermined duration of time, wherein said communicating the fourth command signal to decrease the duty cycle of the motor to the idle state duty cycle is based at least in part on a determination that a second predetermined duration of time has elapsed since the motor-stall-threshold was satisfied.

Clause 42. The method of Clause 41, wherein the second pre-determined duration of time comprises between 20 ms and 150 ms.

Clause 43. The method of Clause 41, wherein the second pre-determined duration of time comprises 80 ms.

Clause 44. The method of any of the previous clauses, further comprising communicating a fifth command signal to provide a series of pulses to the motor.

Clause 45. The method of Clauses 44, wherein communicating the fifth command signal is based at least in part on a determination that the first predetermined duration of time has lapsed.

Clause 46. The method of any of Clauses 44 or 45, wherein said communicating the fifth command signal is further based at least in part on a determination that a motor-stall-threshold is satisfied.

Clause 47. The method of any of Clauses 44 to 46, wherein said communicating the fifth command signal is further based at least in part on a determination that a sensor signal from a myoelectric sensor satisfies a sensor grip threshold.

Clause 48. The method of Clauses 47, wherein the sensor grip threshold corresponds to a user engaging a muscle of the wearer of the prosthetic device for a third predetermined duration of time.

Clause 49. The method of Clauses 48, wherein the third predetermined duration of time comprises 500 milliseconds.

Clause 50. The method of Clauses 44, wherein the series of pulses are communicated to the motor over a one second time interval.

Clause 51. The method of any of the previous clauses, further comprising:

based at least in part on a determination that that the finger digit satisfies a location threshold with respect to the second position, communicating one or more command signals to systematically decrease a duty cycle of the motor until the finger digit reaches the second position.

Clause 52. The method of Clause 51, further comprising:

receiving one or more sensors signals from a position sensor, and determining a real-time position of the finger digit based at least in part on the one or more sensor signals, wherein said determining that the finger digit satisfies the location threshold with respect to the second position is based at least in part on the real-time position of the finger digit.

Clause 53. The method of Clause 52, wherein the position sensor comprises a Hall Effect sensor.

Clause 54. The method of any of Clauses 51 to 53, wherein the systematic decrease occurs over a predetermined duration of time.

Clause 55. The method of any of Clauses 51 to 54, wherein the systematic decrease reduces the duty cycle to an idle state duty cycle when the finger digit reaches the second position.

Clause 56. The method of any of Clauses 51 to 55, wherein the systematic decrease comprises a linear decrease.

Clause 57. The method of any of Clauses 51 to 56, wherein the systematic decrease comprises a uniform decrease.

Clause 58. The method of any of Clauses 51 to 57, wherein the systematic decrease comprises a non-uniform decrease.

Clause 59. The method of any of Clauses 51 to 58, wherein the systematic decrease comprises a stepwise decrease.

Clause 60. The method of any of Clauses 51 to 59, wherein the systematic decrease corresponds to a reverse S-shaped decay curve.

Clause 61. The method of any of Clauses 51 to 60, wherein the systematic increase corresponds to a reverse J-shaped decay curve.

Example Embodiments

Various example embodiments of methods, systems or non-transitory computer-readable medium relating to reducing electromagnetic interference or conserving power in a prosthetic device can be found in the following clauses:

Clause 1. A prosthetic device, comprising:
a finger digit;
a motor configured to move the finger digit based at least in part on one or more command signals received from a controller, wherein the controller is configured to:
determine, based at least in part on a command signal, to move the finger digit from a first position to a second position, and
based at least in part on a determination that that the finger digit satisfies a location threshold with respect to the second position, communicate one or more command signals to systematically decrease a duty cycle of the motor until the finger digit reaches the second position.

Clause 2. The prosthetic device of Clause 1, wherein the controller is further configured to:
receive one or more sensors signals from a position sensor, and determine a real-time position of the finger digit based at least in part on the one or more sensor signals,
wherein the determination that the finger digit satisfies the location threshold with respect to the second position is based at least in part on the real-time position of the finger digit.

Clause 3. The prosthetic device of any of the previous Clauses, further comprising a position sensor usable to identify a position of the finger digit.

Clause 4. The prosthetic device of Clause 3, wherein the position sensor comprises a Hall Effect sensor.

Clause 5. The prosthetic device of any of the previous Clauses, wherein the systematic decrease occurs over a predetermined duration of time.

Clause 6. The prosthetic device of any of the previous Clauses, wherein the systematic decrease comprises a linear decrease.

Clause 7. The prosthetic device of any of the previous Clauses, wherein the systematic decrease comprises a uniform decrease.

Clause 8. The prosthetic device of any of the previous Clauses, wherein the systematic decrease comprises a non-uniform decrease.

Clause 9. The prosthetic device of any of the previous Clauses, wherein the systematic decrease comprises a stepwise decrease.

Clause 10. The prosthetic device of any of the previous Clauses, wherein the systematic decrease corresponds to a reverse S-shaped decay curve.

Clause 11. The prosthetic device of any of the previous Clauses, wherein the systematic increase corresponds to a reverse J-shaped decay curve.

Clause 12. The prosthetic device of any of the previous Clauses, wherein the systematic decrease reduces the duty cycle to an idle state duty cycle when the finger digit reaches the second position.

Clause 13. The prosthetic device of Clause 12, wherein the idle state duty cycle corresponds to a value of duty cycle below 20%.

Clause 14. The prosthetic device of Clause 12, wherein the idle state duty cycle corresponds to a value of duty cycle below 10%.

Clause 15. The prosthetic device of Clause 12, wherein the idle state duty cycle corresponds to a value of duty cycle below 5%.

Clause 16. The prosthetic device of Clause 12, wherein the idle state duty cycle corresponds to a 0% duty cycle.

Example Embodiments

Various example embodiments of methods, systems or non-transitory computer-readable medium relating to reducing electromagnetic interference or conserving power in a prosthetic device can be found in the following clauses:

Clause 1. A method of conserving power in a powered prosthetic device comprising a finger digit and a motor configured to move the finger digit, the method comprising:
determining, based at least in part on a command signal, to move the finger digit from a first position to a second position, and based at least in part on a determination that that the finger digit satisfies a location threshold with respect to the second position, communicating one or more command signals to systematically decrease a duty cycle of the motor until the finger digit reaches the second position.

Clause 2. The method of Clause 1, further comprising:
receiving one or more sensors signals from a position sensor, and determining a real-time position of the finger digit based at least in part on the one or more sensor signals, wherein the determination that the finger digit satisfies the location threshold with respect to the second position is based at least in part on the real-time position of the finger digit.

Clause 3. The method of any of the previous clauses, wherein the position sensor is usable to identify a position of the finger digit.

Clause 4. The method of Clause 3, wherein the position sensor comprises a Hall Effect sensor.

Clause 5. The method of any of the previous Clauses, wherein the systematic decrease occurs over a predetermined duration of time.

Clause 6. The method of any of the previous Clauses, wherein the systematic decrease comprises a linear decrease.

Clause 7. The method of any of the previous Clauses, wherein the systematic decrease comprises a uniform decrease.

Clause 8. The method of any of the previous Clauses, wherein the systematic decrease comprises a non-uniform decrease.

Clause 9. The method of any of the previous Clauses, wherein the systematic decrease comprises a stepwise decrease.

Clause 10. The method of any of the previous Clauses, wherein the systematic decrease corresponds to a reverse S-shaped decay curve.

Clause 11. The method of any of the previous Clauses, wherein the systematic increase corresponds to a reverse J-shaped decay curve.

Clause 12. The method of any of the previous Clauses, wherein the systematic decrease reduces the duty cycle to an idle state duty cycle when the finger digit reaches the second position.

Clause 13. The method of Clause 12, wherein the idle state duty cycle corresponds to a value of duty cycle below 20%.

Clause 14. The method of Clause 12, wherein the idle state duty cycle corresponds to a value of duty cycle below 10%.

Clause 15. The method of Clause 12, wherein the idle state duty cycle corresponds to a value of duty cycle below 5%.

Clause 16. The method of Clause 12, wherein the idle state duty cycle corresponds to a 0% duty cycle.

Terminology

Although this disclosure has been described in the context of certain cases and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may include, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some cases, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain cases include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain cases require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain cases, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A powered prosthetic device, comprising:
a prosthetic finger;
a motor configured to move the prosthetic finger based at least in part on one or more control signals received from a controller, wherein the controller is configured to:
determine, based at least in part on a command signal, to move the prosthetic finger from a first position to a second position,
communicate a first control signal to alter a duty cycle of the motor to satisfy a first duty cycle level to overcome stiction associated with one or more components of the motor, and
based at least in part on a determination that the duty cycle of the motor satisfies the first duty cycle level, communicate a second control signal to systematically increase the duty cycle of the motor over a predetermined duration of time to satisfy a second duty cycle level.

2. The device of claim 1, further comprising a myoelectric sensor configured to sense electric activity of a muscle of a user, wherein the controller is further configured to receive sensor signals from the myoelectric sensor, wherein the command signal corresponds to one or more of the sensor signals from the myoelectric sensor.

3. The device of claim 1, wherein the first position corresponds to an open position and the second position corresponds to a closed position.

4. The device of claim 1, wherein the controller is further configured to:
based at least in part on a determination that the predetermined duration of time has lapsed, communicate one or more third control signals to vary the duty cycle of the motor in proportion to one or more sensor signals received from a myoelectric sensor.

5. The device of claim 4, wherein the controller is further configured to:
based at least in part on a determination that the predetermined duration of time has lapsed and a determination that a torque of the motor satisfies a torque threshold, communicate a fourth control signal to decrease the duty cycle of the motor to an idle state duty cycle.

6. The device of claim 4, wherein the predetermined duration of time is a first predetermined duration of time, wherein the controller is further configured to:
based at least in part on a determination that the first predetermined duration of time has lapsed and a determination that a torque of the motor satisfies a torque threshold, communicate a fourth control signal to decrease the duty cycle of the motor to an idle state duty cycle after an expiration of a second predetermined duration of time.

7. The device of claim 6, wherein the controller is further configured to determine that the torque threshold is satisfied based at least in part on a determination that a current drawn by the motor from a power source satisfies a current threshold.

8. The device of claim 1, wherein the controller is further configured to:
based at least in part on a determination that the predetermined duration of time has lapsed, a determination that a torque of the motor satisfies a torque threshold, and a determination that a sensor signal from a myoelectric sensor satisfies a sensor grip threshold, communicate one or more third control signals to increase a grip force of the prosthetic finger on an object.

9. The device of claim 8, wherein the sensor grip threshold corresponds to a user engaging a muscle of the user for a second predetermined duration of time.

10. The device of claim 1, wherein the controller is configured to:
based at least in part on a determination that the prosthetic finger satisfies a location threshold with respect to the second position, communicate one or more third control signals to systematically decrease the duty cycle of the motor until the prosthetic finger reaches the second position.

11. The device of claim 10, wherein the controller is further configured to:
receive one or more sensors signals from a position sensor usable to identify a position of the prosthetic finger, and
determine a real time position of the prosthetic finger based at least in part on the one or more sensor signals,
wherein the determination that the prosthetic finger satisfies the location threshold with respect to the second position is based at least in part on the position of the prosthetic finger.

12. A method of reducing electromagnetic interference or conserving power in a powered prosthetic device comprising a prosthetic finger and a motor configured to move the prosthetic finger, wherein the method comprises:
determining, based at least in part on a command signal, to move a prosthetic finger from a first position to a second position via a motor;
communicating a first control signal to alter a duty cycle of the motor to satisfy a first duty cycle level to overcome stiction associated with one or more components of the motor; and
based at least in part on a determination that the duty cycle of the motor satisfies the first duty cycle level, communicating a second control signal to systematically increase the duty cycle of the motor over a predetermined duration of time to satisfy a second duty cycle level.

13. The method of claim 12, further comprising:
receiving sensor signals from a myoelectric sensor configured to sense electric activity of a muscle of a user, wherein the command signal corresponds to one or more of the sensor signals from the myoelectric sensor.

14. The method of claim 12, wherein the first position corresponds to an open position and the second position corresponds to a closed position.

15. The method of claim 12, further comprising:
based at least in part on a determination that the predetermined duration of time has lapsed, communicating one or more third control signals to vary the duty cycle of the motor in proportion to one or more sensor signals received from a myoelectric sensor.

16. The method of claim 15, further comprising:
based at least in part on a determination that the predetermined duration of time has lapsed and a determination that a torque of the motor satisfies a torque threshold, communicating a fourth control signal to decrease the duty cycle of the motor to an idle state duty cycle.

17. The method of claim 15, wherein the predetermined duration of time is a first predetermined duration of time, the method further comprising:
based at least in part on a determination that the first predetermined duration of time has lapsed and a determination that a torque of the motor satisfies a torque threshold, communicating a fourth control signal to decrease the duty cycle of the motor to an idle state duty cycle after an expiration of a second predetermined duration of time.

18. The method of claim 12, further comprising:
based at least in part on a determination that the predetermined duration of time has lapsed, a determination that a torque of the motor satisfies a torque threshold, and a determination that a sensor signal from a myoelectric sensor satisfies a sensor grip threshold, communicating one or more third control signals to increase a grip force of the prosthetic finger on an object.

19. The method of claim 12, further comprising:
based at least in part on a determination that the prosthetic finger satisfies a location threshold with respect to the second position, communicating one or more third control signals to systematically decrease the duty cycle of the motor until the prosthetic finger reaches the second position.

20. The method of claim 19, further comprising:
receiving one or more sensors signals from a position sensor usable to identify a position of the prosthetic finger, and
determining a real time position of the prosthetic finger based at least in part on the one or more sensor signals,
wherein the determination that the prosthetic finger satisfies the location threshold with respect to the second position is based at least in part on the position of the prosthetic finger.

* * * * *